United States Patent
Lohray et al.

[11] Patent Number: 6,030,973
[45] Date of Patent: Feb. 29, 2000

[54] HETEROCYCLIC COMPOUNDS HAVING ANTIDIABETIC HYPOLIPIDEMIA AND ANTIHYPERTENSIVE PROPERTIES, PROCESS FOR THEIR PREPARATION AND PHARMACEUTICAL COMPOSITIONS CONTAINING THEM

[75] Inventors: Vidya Bhushan Lohray; Braj Bhushan Lohray, both of Jubilee Hills; Rao Bheema Paraselli, Hyderabad; Rajagopalan Ramanujam, Hyderabad; Ranjan Chakrabarti, Hyderabad, all of India

[73] Assignees: Dr. Reddy's Research Foundation, Hyderabad, India; Reddy-Cheminor, Inc., Ridgewood, N.J.

[21] Appl. No.: 09/135,566

[22] Filed: Aug. 17, 1998

Related U.S. Application Data

[62] Division of application No. 08/982,911, Dec. 2, 1997, abandoned.

[30] Foreign Application Priority Data

Apr. 15, 1997 [IN] India ................ 771/MAS/97

[51] Int. Cl.⁷ ............ A61K 31/505; C07D 239/91; C07D 239/92; C07D 265/22; C07D 279/08
[52] U.S. Cl. ............. 514/259; 544/284; 544/285; 544/286; 544/287; 544/288; 544/290; 544/116; 544/73; 544/92; 544/93; 544/50; 544/253; 544/254; 544/230.5; 544/224.2
[58] Field of Search ............... 544/286, 284, 544/285, 287, 288, 290; 514/259

[56] References Cited

U.S. PATENT DOCUMENTS

| | | | |
|---|---|---|---|
| 4,873,255 | 10/1989 | Yoshioka | 514/369 |
| 5,002,953 | 3/1991 | Hindley | 514/275 |
| 5,037,842 | 8/1991 | Goldstein | 514/375 |
| 5,468,762 | 11/1995 | Malamas | 514/376 |
| 5,478,851 | 12/1995 | Cantello | 514/369 |
| 5,478,852 | 12/1995 | Olefsky | 514/369 |
| 5,478,853 | 12/1995 | Regnier | 514/369 |
| 5,521,201 | 5/1996 | Hindley | 514/342 |
| 5,710,152 | 1/1998 | Nagao et al. | 514/225.2 |
| 5,885,997 | 3/1999 | Lohray et al. | 514/256 |

FOREIGN PATENT DOCUMENTS

| | | |
|---|---|---|
| 0139421 | 5/1985 | European Pat. Off. . |
| 0306228 | 3/1989 | European Pat. Off. . |
| 0419035 | 3/1991 | European Pat. Off. . |
| 0604983 | 7/1994 | European Pat. Off. . |
| 0612743 | 8/1994 | European Pat. Off. . |
| 0676398 | 10/1995 | European Pat. Off. . |
| 0678511 | 10/1995 | European Pat. Off. . |
| 0745600 | 12/1996 | European Pat. Off. . |
| 0783888 | 7/1997 | European Pat. Off. . |
| 0787727 | 8/1997 | European Pat. Off. . |
| 0912575 | 1/1997 | Japan . |
| 9112003 | 8/1991 | WIPO . |
| 9207838 | 5/1992 | WIPO . |
| 9425026 | 11/1994 | WIPO . |
| 9507697 | 3/1995 | WIPO . |
| 9521608 | 8/1995 | WIPO . |
| 9526347 | 8/1995 | WIPO . |
| 9535108 | 12/1995 | WIPO . |
| 9605186 | 2/1996 | WIPO . |
| 9611196 | 4/1996 | WIPO . |
| 9626207 | 8/1996 | WIPO . |
| 9741097 | 11/1997 | WIPO . |

OTHER PUBLICATIONS

M. Modan, et al., J. Clin. Invest. (1985) vol. 75, pp. 809–817.
O. G. Kolterman, et al., J. Clin. Invest. (1981) vol. 68, pp. 957–969.
E. Ferrannini, et al., The New England Journal of Medicine (1987) vol. 317, pp. 350–357.
D.C. Shen, et al., J. Clin. Endocrinol. Metab. (1988) vol. 66, pp. 580–583.
Goodman & Gilman's The Pharmacological Basis of Therapeutics, Ninth Ediition, pp. 1496–1497.
Clifford Bailey, "Potential New Treatments for Type 2 Diabetes", Chemistry & Industry, Jan. 19, 1998, pp. 53–57.
T. Antonucci, et al., "Imparied Glucose Tolerance is Normalized by Treatment with the ThiazolidinedioneTroglitazone" Diabetes Care, vol. 20, No. 2, Feb. 1997, pp. 188–193.Messier, C. et al., Behavioral Brain Research, 75 (1966) 1–11.

(List continued on next page.)

*Primary Examiner*—Mukund J. Shah
*Assistant Examiner*—Ann M. Kessinger
*Attorney, Agent, or Firm*—Ladas & Parry

[57] ABSTRACT

The present invention relates to novel antidiabetic compounds, their tautomeric forms, their derivatives, their analogues, their stereoisomers, their polymorphs, their pharmaceutically acceptable salts, their pharmaceutically acceptable solvates and pharmaceutically acceptable compositions containing them. This invention particularly relates to novel azolidinediones of the general formula (I), their analogues, their derivatives, their tautomeric forms, their stereoisomers, their polymorphs, their pharmaceutically acceptable salts, pharmaceutically acceptable solvates and pharmaceutical compositions containing them.

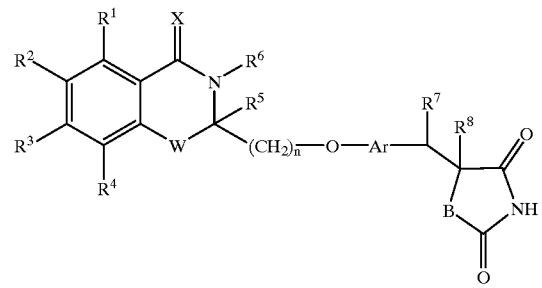

(I)

22 Claims, No Drawings

OTHER PUBLICATIONS

Sohda, T. et al., Chem Pharm Bull. 30, 10 (1982), 3580–3600.
Clark, et al. J. Med. Chem 34 (1991) 319–325.
Dow, R. L. et al., J. Med. Chem 34 (1991) 1538–1544.
Hulin, et al., J. Med. Chem 35 (1992) 1853–1864.
Sohda, T. et al., J. Med. Chem 35 (1992) 2617–2626.
Goldstein, et al., J. Med. Chem. 36 (1993) 2238–2240.

Cantello, et al., J. Med. Chem 37 (1994) 3977–3985.

English Translation of JP–A–0912575.

Husain M.I. et al: "Some New 2–Aryloxymethyl–3–Alpha–Substituted Carboxymethyl–6, 8–Substituted 4–Quinazolones as Possible Anticonvulsants" Pharmazie, vol. 37, No. 6, 1982, pp. 408–410, XP002045115.

HETEROCYCLIC COMPOUNDS HAVING ANTIDIABETIC HYPOLIPIDEMIA AND ANTIHYPERTENSIVE PROPERTIES, PROCESS FOR THEIR PREPARATION AND PHARMACEUTICAL COMPOSITIONS CONTAINING THEM

This application is a divisional of U.S. patent application Ser. No. 08/982,911, filed Dec. 2, 1997, now abandoned.

FIELD OF THE INVENTION

The present invention relates to novel antidiabetic compounds, their tautomeric forms, their derivatives, their analogues, their stereoisomers, their polymorphs, their pharmaceutically acceptable salts, their pharmaceutically acceptable solvates and pharmaceutically acceptable compositions containing them. This invention particularly relates to novel azolidinediones of the general formula (I), their analogues, their derivatives, their tautomeric forms, their stereoisomers, their polymorphs, their pharmaceutically acceptable salts, pharmaceutically acceptable solvates and pharmaceutical compositions containing them.

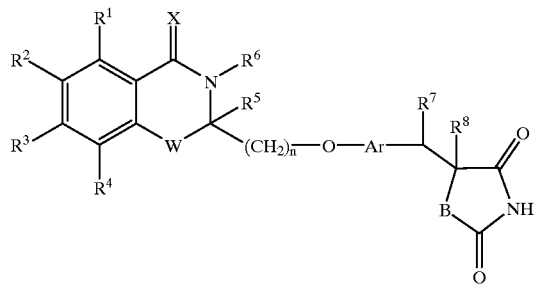

(I)

The present invention also relates to a process for the preparation of the above said novel azolidinedione compounds, derivatives, analogues, tautomeric forms, stereoisomers, polymorphs, pharmaceutically acceptable salts, and pharmaceutically acceptable solvates; and pharmaceutical compositions containing them.

This invention also relates to novel intermediates, processes for preparing the intermediates and processes for using the intermediates.

The azolidinediones of the general formula (I) defined above of the present invention are useful for the treatment and/or prophylaxis of hyperlipidemia, hypercholesterolemia, hyperglycemia, osteoporosis, obesity, glucose intolerance, insulin resistance and also diseases or conditions in which insulin resistance is the underlying pathophysiological mechanism. Examples of these diseases and conditions are type II diabetes, impaired glucose tolerance, dyslipidaemia, hypertension, coronary heart disease and other cardiovascular disorders including atherosclerosis. The azolidinediones of formula (I) are useful for the treatment of insulin resistance associated with obesity and psoriasis. The azolidinediones of the formula (I) can also be used to treat diabetic complications and can be used for treatment and/or prophylaxis of other diseases and conditions such as polycystic ovarian syndrome (PCOS), certain renal diseases including diabetic nephropathy, glomerulonephritis, glomerular sclerosis, nephrotic syndrome, hypertensive nephrosclerosis, end-stage renal diseases and microalbuminuria as well as certain eating disorders, as aldose reductase inhibitors and for improving cognitive functions in dementia.

BACKGROUND OF THE INVENTION

Insulin resistance is the diminished ability of insulin to exert its biological action across a broad range of concentrations. In insulin resistance, the body secretes abnormally high amounts of insulin to compensate for this defect; failing which, the plasma glucose concentration inevitably rises and develops into diabetes. Among the developed countries, diabetes mellitus is a common problem and is associated with a variety of abnormalities including obesity, hypertension, hyperlipidemia (J. Clin. Invest., (1985) 75: 809–817; N. Engl. J. Med. (1987) 317: 350–357; J. Clin. Endocrinol. Metab., (1988) 66: 580–583; J. Clin. Invest., (1975) 68: 957–969) and other renal complications (See patent application Ser. No. WO 95/21608). It is now increasingly being recognized that insulin resistance and relative hyperinsulinemia have a contributory role in obesity, hypertension, atherosclerosis and type 2 diabetes mellitus. The association of insulin resistance with obesity, hypertension and angina has been described as a syndrome having insulin resistance as the central pathogenic link-Syndrome-X. In addition, polycystic ovarian syndrome (patent application Ser. No. WO 95/07697), psoriasis (patent application Ser. No. WO 95/35108), dementia (Behavioral Brain Research (1996) 75: 1–11) etc. may also have insulin resistance as a central pathogenic feature. Recently, it has also been reported that insulin sensitizers improve the bone mineral density and thus may be useful for the treatment of osteoporosis (EP-783888).

A number of molecular defects have been associated with insulin resistance. These include reduced expression of insulin receptors on the plasma membrane of insulin responsive cells and alterations in the signal transduction pathways that become activated after insulin binds to its receptor including glucose transport and glycogen synthesis.

Since defective insulin action is thought to be more important than failure of insulin secretion in the development of non-insulin dependent diabetes mellitus and other related complications, this raises doubts about the intrinsic suitability of antidiabetic treatment that is based entirely upon stimulation of insulin release. Recently, Takeda has developed a new class of compounds which are the derivatives of 5-(4-alkoxybenzyl)-2,4-thiazolidinediones of the formula (II) (Ref. *Chem. Pharm. Bull.* 1982, 30, 3580–3600). In the formula (II), V represents substituted or unsubstituted divalent aromatic group B represents a sulfur atom or an oxygen atom and U represents various groups which have been reported in various patent documents.

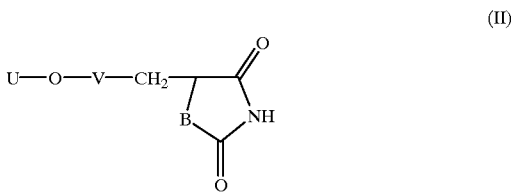

(II)

By way of examples, U may represent the following groups:
(i) a group of the formula (IIa) where $R^1$ is hydrogen or hydrocarbon residue or heterocyclic residue which may each be substituted, $R^2$ is hydrogen or a lower alkyl which may be substituted by hydroxy group, X is an oxygen or sulphur atom, Z is a hydroxylated methylene or a carbonyl, m is 0 or 1, n is an integer of 1–3. These compounds have been disclosed in the European Patent Application No. 0 177 353

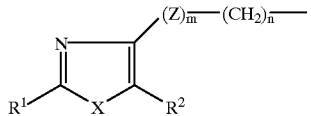
(IIa)

An example of these compounds is shown in formula (IIb)

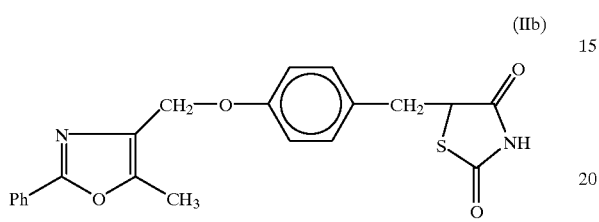
(IIb)

(ii) a group of the formula (IIc) wherein $R^1$ and $R^2$ are the same or different and each represents hydrogen or $C_1$–$C_5$ alkyl, $R^3$ represents hydrogen, acyl group, a ($C_1$–$C_6$) alkoxycarbonyl group or aralkyloxycarbonyl group, $R^4$–$R^5$ are same or different and each represent hydrogen, $C_1$–$C_5$ alkyl or $C_1$–$C_5$ alkoxy or $R^4$, $R^5$ together represent $C_1$–$C_4$ alkenedioxy group, n is 1, 2, or 3, W represents $CH_2$, CO, $CHOR^6$ group in which $R^6$ represents any one of the items or groups defined for $R^3$ and may be the same or different from $R^3$. These compounds are disclosed in the European Patent Application No. 0 139 421.

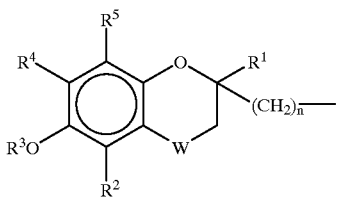
(IIc)

An example of these compounds is shown in (IId)

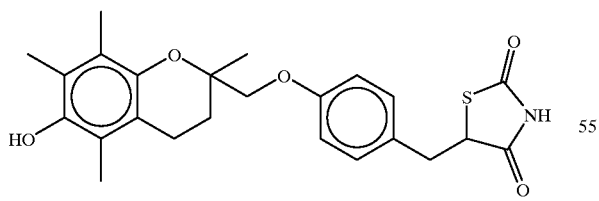
(IId)

iii) A group of formula (IIe) where $A^1$ represents substituted or unsubstituted aromatic heterocyclic group, $R^1$ represents a hydrogen atom, alkyl group, acyl group, an aralkyl group wherein the aryl moiety may be substituted or unsubstituted, or a substituted or unsubstituted aryl group, n represents an integer in the range from 2 to 6. These compounds are disclosed in European Patent No. 0 306 228.

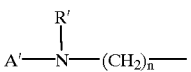
(IIe)

An example of this compound is shown in formula (IIf)

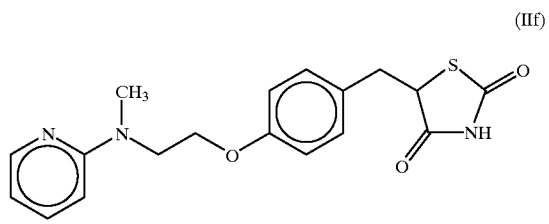
(IIf)

iv) A group of formula (IIg) where Y represents N or $CR^5$, $R^1$, $R^2$, $R^3$, $R^4$ and $R^5$ represents hydrogen, halogen, alkyl and the like and $R^6$ represents hydrogen, alkyl, aryl and the like, n represents an integer of 0 to 3. These compounds are disclosed in European Patent Application No. 0 604 983.

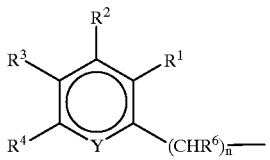
(IIg)

An example of this compound is shown in formula (IIh)

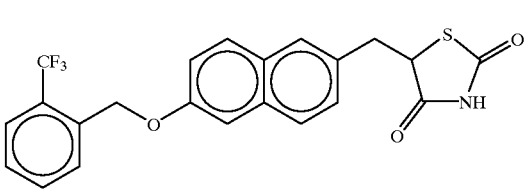
(IIh)

v) a group of formula (IIi), where R is ($C_1$–$C_6$) alkyl groups, cycloalkyl group, furyl, thienyl, substituted or unsubstituted phenyl group, X is hydrogen, methyl, methoxy, chloro or fluoro. These compounds have been disclosed in the U.S. Pat. No. 5,037,842.

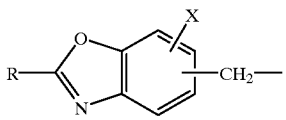
(IIi)

An example of these compounds is shown in formula (IIj).

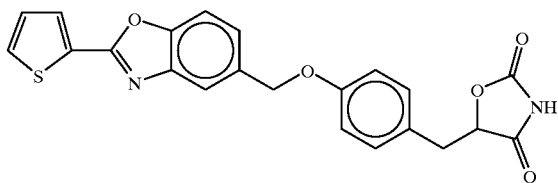

(IIj)

(vi) a group of formula (IIk) wherein $A^1$ represents a substituted or unsubstituted aromatic heterocyclyl group; $R^1$ represents a hydrogen atom, an alkyl group, an acyl group, an aralkyl group, wherein the aryl moiety may be substituted or unsubstituted or a substituted or unsubstituted aryl group, n represents an integer in the range of from 2 to 6. These compounds have been disclosed in the patent application No. WO 92/02520.

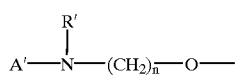

(IIk)

An example of these compounds is shown in formula (II I).

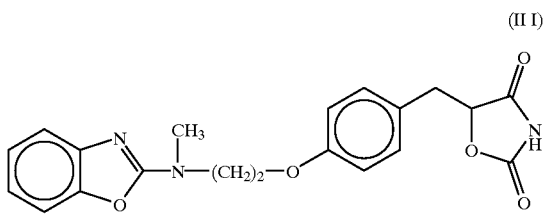

(II I)

Some of the above referenced hitherto known antidiabetic compounds seem to possess bone marrow depression, liver and cardiac toxicities and modest potency and consequently, their regular use for the treatment and control of diabetes is becoming limited and restricted.

SUMMARY OF THE INVENTION

With an objective of developing new compounds for the treatment of type II diabetes [non-insulin-dependent-diabetes mellitus (NIDDM)] which could be more potent at relatively lower doses and having better efficacy with lower toxicity, we focused our research efforts in a direction of incorporating safety and to have better efficacy, which has resulted in the development of novel azolidinedione compounds having the general formula (I) as defined above.

The main objective of the present invention is therefore, to provide novel azolidinediones, their derivatives, their analogues, their tautomeric forms, their stereoisomers, their polymorphs, their pharmaceutically acceptable salts, their pharmaceutically acceptable solvates and pharmaceutical compositions containing them and mixtures thereof.

Another objective of the present invention is to provide novel azolidinedione compounds, their derivatives, their analogues, their tautomeric forms, their stereoisomers, their polymorphs, their pharmaceutically acceptable salts, their pharmaceutically acceptable solvates and pharmaceutical compositions containing them and mixtures thereof having enhanced activities, no toxic effect or reduced toxic effect.

Yet another objective of the present invention is to provide a process for the preparation of novel azolidinediones of the formula (I) as defined above, their tautomeric forms, their analogues, their derivatives, their stereoisomers, their polymorphs, their pharmaceutically acceptable salts and their pharmaceutically acceptable solvates.

Still another objective of the present invention is to provide pharmaceutical compositions containing compounds of the general formula (I), their tautomers, their stereoisomers, their derivatives, their analogues, their polymorphs, their salts, solvates or mixtures thereof in combination with suitable carriers, solvents, diluents, excipients and other media normally employed in preparing such compositions.

Yet another objective of the present invention is to provide novel intermediates of the formula (III)

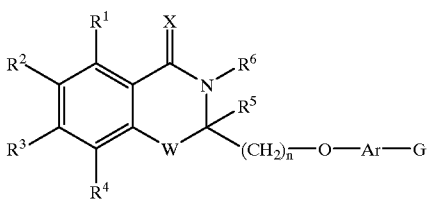

(III)

where G represents —CHO, —NO$_2$, —NH$_2$ or —CH$_2$CH(J)—COOR, where J represents halogen atom such as chlorine, bromine or iodine and R represents H or lower alkyl group such as ($C_1$–$C_6$) alkyl group, preferably a ($C_1$–$C_3$) alkyl group such as methyl, ethyl, or propyl; and $R^1$, $R^2$, $R^3$, $R^4$, $R^5$, $R^6$, X, W, n and Ar are defined as in formula (I).

Still another objective of the present invention is to provide a process for the preparation of the novel intermediates of the formula (III)

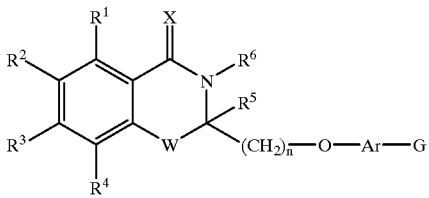

(III)

where G represents —CHO, —NO$_2$, —NH$_2$ or —CH$_2$CH(J)—COOR, where J represents halogen atom such as chlorine, bromine or iodine and R represents H or lower alkyl group such as ($C_1$–$C_6$) alkyl group, preferably a ($C_1$–$C_3$) alkyl group such as methyl, ethyl, or propyl; and $R^1$, $R^2$, $R^3$, $R^4$, $R^5$, $R^6$, X, W, n and Ar are defined as in formula (I).

DETAILED DESCRIPTION OF THE INVENTION

Azolidinediones of the present invention have the general formula (I)

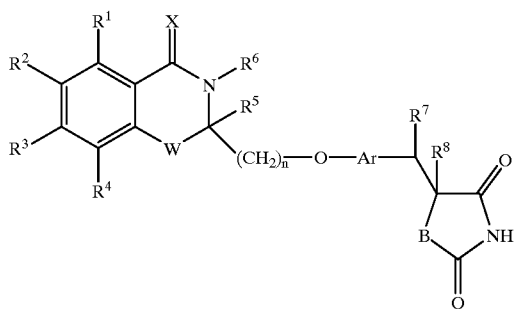

(I)

In the above formula (I), X represents O or S; the groups $R^1$, $R^2$, $R^3$, $R^4$ may be same or different and represent hydrogen, halogen, hydroxy, cyano, nitro; optionally substituted groups selected from alkyl, cycloalkyl, alkoxy, cycloalkyloxy, aryl, aralkyl, heteroaryl, heteroaralkyl, heterocyclyl, aryloxy, alkoxycarbonyl, aryloxycarbonyl, aralkoxycarbonyl, alkylamino, arylamino, amino, aminoalkyl, hydroxyalkyl, alkoxyalkyl, thioalkyl, alkylthio, acyl, acylamino, aryloxycarbonylamino, aralkoxycarbonylamino, alkoxycarbonylamino, carboxylic acid or its derivatives, acyloxy, sulfonic acid or its derivatives; W represents O, S or a group $NR^9$; $R^6$ and $R^9$ may be same or different and represent hydrogen; or optionally substituted alkyl, cycloalkyl, aryl, aralkyl, heterocyclyl, heteroaryl, heteroaralkyl, acyl, hydroxyalkyl, aminoalkyl, alkoxycarbonyl, aryloxycarbonyl, aralkoxycarbonyl, alkoxyalkyl, alkylthio, or thioalkyl groups; $R^5$ represents hydrogen, hydroxy, or halogen atom or optionally substituted alkyl, aryl, heteroaryl, acyl, alkoxy, aralkyl, or aralkoxy; n is an integer ranging from 1–4; Ar represent an optionally substituted divalent aromatic or heterocyclic group; $R^7$ and $R^8$ may be same or different and individually represents hydrogen atom, halogen, hydroxy, lower alkyl, optionally substituted aralkyl group or together form a bond; and B represents an oxygen atom or a sulfur atom.

Suitable groups represented by $R^1$, $R^2$, $R^3$, $R^4$ may be selected from hydrogen, halogen atom such as fluorine, chlorine, bromine, or iodine; hydroxy, cyano, nitro; substituted or unsubstituted ($C_1$–$C_{12}$)alkyl group, especially, linear or branched ($C_1$–$C_6$)alkyl group, such as methyl, ethyl, n-propyl, isopropyl, n-butyl, iso-butyl, t-butyl, n-pentyl, isopentyl, hexyl and the like; cycloalkyl group such as cyclopropyl, cyclobutyl, cyclopentyl, cyclohexyl and the like, cycloalkyl group may be substituted; cycloalkyloxy group such as cyclopropyloxy, cyclobutyloxy, cyclopentyloxy, cyclohexyloxy and the like, cycloalkyloxy group may be substituted; aryl group such as phenyl or naphthyl, the aryl group may be substituted; aralkyl such as benzyl or phenethyl, the aralkyl group may be substituted; heteroaryl group such as pyridyl, thienyl, furyl, pyrrolyl, oxazolyl, thiazolyl, imidazolyl, oxadiazolyl, tetrazolyl, benzopyranyl, benzofuranyl and the like, the heteroaryl group may be substituted; heteroaralkyl wherein the heteroaryl moiety is as defined earlier and is attached to ($C_1$–$C_3$) alkylene group such as furanmethyl, pyridinemethyl, oxazolemethyl, oxazolethyl, and the like, the heteroaralkyl group may be substituted; heterocyclyl groups such as aziridinyl, pyrrolidinyl, morpholinyl, piperidinyl, piperazinyl and the like, the heterocyclyl group may be substituted; aryloxy such as phenoxy, naphthyloxy, the aryloxy group may be substituted; alkoxycarbonyl such as methoxycarbonyl or ethoxycarbonyl, the alkoxycarbonyl group may be substituted; aryloxycarbonyl group such as optionally substituted phenoxycarbonyl or naphthyloxycarbonyl; substituted or unsubstituted aralkoxycarbonyl wherein the aryl moiety is phenyl or naphthyl, such as benzyloxycarbonyl, phenethyloxycarbonyl, naphthylmethyloxycarbonyl and the like; linear or branched ($C_1$–$C_6$) alkylamino; arylamino group such as $HNC_6H_5$; —$NCH_3C_6H_5$; —$NHC_6H_4$—$CH_3$, —$NHC_6H_4$—halo and the like, amino group; amino $C_1$–$C_6$)alkyl; hydroxy($C_1$–$C_6$)alkyl; ($C_1$–$C_6$) alkoxy; alkoxyalkyl such as methoxymethyl, ethoxymethyl, methoxyethyl and the like; thio($C_1$–$C_6$)alkyl; ($C_1$–$C_6$) alkylthio; acyl group such as acetyl, propionyl or benzoyl, the acyl group may be substituted; acylamino groups such as $NHCOCH_3$, $NHCOC_2H_5$, $NHCOC_3H_7$, $NHCOC_6H_5$, aralkoxycarbonylamino group such as $NHCOOCH_2C_6H_5$— $NHCOOCH_2CH_2C_6H_5$, —$NCH_3COOCH_2C_6H_5$,— $NC_2H_5COOCH_2C_6H_5$, —$NHCOOCH_2C_6H_4CH_3$, —$NHCOOCH_2C_6H_4OCH_3$ and the like, alkoxycarbonyl amino group such as $NHCOOC_2H_5$, $NHCOOCH_3$ and the like; aryloxycarbonylamino group such as $NHCOOC_6H_5$, —$NCH_3COOC_6H_5$, —$NC_2H_5COOC_6H_5$, —$NHCOOC_6H_4CH_3$, —$NHCOOC_6H_4OCH_3$ and the like; carboxylic acid or its derivatives such as amides, like $CONH_2$, CONHMe, $CONMe_2$, CONHEt, $CONEt_2$, CONHPh and the like, the carboxylic acid derivatives may be substituted; acyloxy group such as MeCOO, EtCOO, PhCOO and the like, which may optionally be substituted; sulfonic acid or its derivatives such as $SO_2NH_2$, $SO_2NHMe$, $SO_2NMe_2$, $SO_2NHCF_3$ and the like, the sulfonic acid derivatives may be substituted.

The alkoxy, alkylamino, arylamino, amino, aminoalkyl, hydroxyalkyl, alkoxyalkyl, thioalkyl, alkylthio, acylamino, aryloxycarbonylamino, aralkoxycarbonylamino, and alkoxycarbonylamino groups may also be substituted.

When the groups represented by $R^1$, $R^2$, $R^3$, $R^4$ are substituted, the substituents may be selected from halogen, hydroxy, cyano, or nitro or optionally substituted groups selected from alkyl, cycloalkyl, alkoxy, cycloalkoxy, aryl, aralkyl, heterocyclyl, heteroaryl, heteroaralkyl, acyl, acyloxy, hydroxyalkyl, amino, acylamino, arylamino, aminoalkyl, aryloxy, alkoxycarbonyl, alkylamino such as $NHCH_3$, $N(CH_3)_2$, $NCH_3(C_2H_5)$, $NHC_2H_5$ and the like; alkoxyalkyl such as methoxymethyl, ethoxymethyl, methoxyethyl and the like; alkylthio, thioalkyl groups, carboxylic acid or its derivatives, or sulfonic acid or its derivatives.

These groups are as defined above for $R^1$–$R^4$.

It is preferred that $R^1$–$R^4$ represent hydrogen; halogen atom such as fluorine, chlorine, bromine; alkyl group such as methyl, ethyl, isopropyl, n-propyl, n-butyl; and the like which may be halogenated; optionally halogenated groups selected from cycloalkyl group such as cyclopropyl; aryl group such as phenyl; aralkyl group such as benzyl; ($C_1$–$C_3$) alkoxy, aryloxy group such as benzyloxy, hydroxy group, acyl or acyloxy groups. Acyl and acyloxy groups are as defined above.

Suitable $R^6$ and $R^9$ are selected from hydrogen, substituted or unsubstituted ($C_1$–$C_{12}$)alkyl group, especially, linear or branched ($C_1$–$C_6$)alkyl group, such as methyl, ethyl, n-propyl, isopropyl, n-butyl, iso-butyl, t-butyl, n-pentyl, isopentyl, hexyl and the like; substituted or unsubstituted cycloalkyl group such as cyclopropyl, cyclobutyl, cyclopentyl, cyclohexyl and the like; aryl group such as phenyl or naphthyl, the aryl group may be substituted; aralkyl group such as benzyl or phenethyl, the aralkyl group may be substituted; heteroaryl group such as pyridyl, thienyl, furyl and the like, the heteroaryl group may be substituted; substituted or unsubstituted heterocyclyl such as aziridinyl, pyrrolidinyl, morpholinyl, piperidinyl and the like; substituted or unsubstituted heteroaralkyl such as pyridylmethyl, furanmethyl, oxazolemethyl, oxazolethyl and the like; substituted or unsubstituted alkoxyalkyl such as methoxymethyl, ethoxymethyl, ethoxyethyl, methoxyethyl and the like; substituted or unsubstituted alkylthio such as $SCH_3$, $SC_2H_5$, $SC_3H_7$ and the like; substituted or unsubstituted alkoxycarbonyl such as methoxycarbonyl or ethoxycarbonyl; aryloxycarbonyl group such as optionally substituted phenoxycarbonyl or naphthyloxycarbonyl; substituted or unsubstituted aralkoxycarbonyl group such as benzyloxycarbonyl, napthylmethoxycarbonyl; amino $(C_1-C_6)$alkyl; hydroxy$(C_1-C_6)$alkyl; thio$(C_1-C_6)$alkyl; and acyl group such as acetyl, propionyl or benzoyl. The acyl, aminoalkyl, hydroxyalkyl and thioalkyl groups may be substituted.

When the groups represented by $R^6$, $R^9$ are substituted, the preferred substituents are halogen such as fluorine, chlorine; hydroxy, acyl, acyloxy, and amino groups.

The acyl and acyloxy groups are as defined above.

Suitable $R^5$ may be hydrogen, halogen, hydroxy or optionally substituted $(C_1-C_6)$alkyl group which may be linear or branched, aryl, heteroaryl, $(C_1-C_6)$alkoxy, aralkyl, aralkoxy, or acyl groups.

$R^5$ may be substituted by hydroxy, halogen, linear or branched $(C_1-C_6)$ alkyl group, acyl or acyloxy group.

These groups are as defined above.

n is an integer ranging from 1–4. It is preferred that n be 1 or 2.

It is preferred that the group represented by Ar be substituted or unsubstituted groups selected from divalent phenylene, naphthylene, pyridyl, quinolinyl, benzofilryl, dihydrobenzofiryl, benzopyranyl, indolyl, indolinyl, azaindolyl, azaindolinyl, pyrazolyl, benzothiazolyl, benzoxazolyl and the like. The substituents on the group represented by Ar may be selected from linear or branched $(C_1-C_6)$alkyl, $(C_1-C_3)$alkoxy, halogen, acyl, amino, acylamino, thio or carboxylic or sulfonic acids and their derivatives.

It is more preferred that Ar represents substituted or unsubstituted divalent phenylene, naphthylene, benzofuryl, indolyl, indolinyl, quinolinyl, azaindolyl, azaindolinyl, benzothiazolyl or benzoxazolyl.

It is still more preferred that Ar represents divalent phetylene or naphthylene, which may be optionally substituted by methyl, halomethyl, methoxy or halomethoxy groups.

Suitable $R^7$ includes hydrogen, hydroxy, lower alkyl group such as $(C_1-C_6)$alkyl such as methyl, ethyl or propyl; substituted or unsubstituted aralkyl group such as benzyl, phenethyl $CH_2C_6H_4$—Halo, $CH_2C_6H_4$—$OCH_3$, $CH_2C_6H_4CH_3$, $CH_2CH_2C_6H_4CH_3$ and the like; halogen atom such as fluorine, chlorine, bromine or iodine; or $R^7$ together with $R^8$ represents a bond.

It is preferred that $R^7$ represents hydrogen or a bond together with $R^8$.

Suitable $R^8$ represents hydrogen, hydroxy, lower alkyl group such as $(C_1-C_6)$alkyl such as methyl, ethyl or propyl; substituted or unsubstituted aralkyl group such as benzyl, phenethyl, $CH_2C_6H_4$—Halo, $CH_2C_6H_4$—$OCH_3$, $CH_2C_6H_4CH_3$, $CH_2CH_2C_6H_4CH_3$ and the like; halogen atom such as fluorine, chlorine, bromine or iodine; or together with $R^7$ forms a bond.

When $R^7$ or $R^8$ is lower alkyl, the lower alkyl may be substituted by groups such as halogen, methyl or oxo group.

Suitable B group includes a hetero atom selected from O or S.

Suitable ring structure comprising B include 2,4-dioxooxazolidinyl, 2,4-dioxothiazolidinyl groups.

It is more preferred that the ring structure comprising B is a 2,4-dioxothiazolidinyl group.

The groups represented by $R^1$–$R^9$ and any substituents on these groups may be defined as disclosed anywhere in the specification.

Pharmaceutically acceptable salts forming part of this invention include salts of the azolidinedione moiety such as alkali metal salts like Li, Na, and K salts, alkaline earth metal salts like Ca and Mg salts, salts of organic bases such as lysine, arginine, guanidine, diethanolamine, choline and the like, ammonium or substituted ammonium salts, salts of carboxy group wherever appropriate, such as aluminum, alkali metal salts; alkaline earth metal salts, ammonium or substituted ammonium salts. Salts may include acid addition salts which are, sulphates, nitrates, phosphates, perchlorates, borates, hydrohalides, acetates, tartrates, maleates, citrates, succinates, palmoates, methanesulfonates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

Particularly useful compounds according to the present invention include:

5-[4-[[4-Oxo-3,4-dihydro-(2H)-1,3-benzoxazine-2-yl]methoxy]phenyl methyl]thiazolidin-2,4-dione;

5-[4-[[3-Methyl-4-oxo-3,4-dihydro-(2H)-1,3-benzoxazine-2-yl]methoxy]phenyl methyl]thiazolidin-2,4-dione;

5-[4-[[3-Ethyl-4-oxo-3,4-dihydro-(2H)-1,3-benzoxazine-2-yl]methoxy]phenyl methyl]thiazolidin-2,4-dione;

5-[4-[2,3-Dimethyl-4-oxo-3,4-dihydro-(2H)-1,3-benzoxazine-2-yl]methoxy]phenyl methyl]thiazolidin-2,4-dione;

5-[4-[[4-Oxo-3,4-dihydro-(2H)-1,3-benzoxazine-2-yl]methoxy]phenyl methyl]thiazolidin-2,4-dione, sodium salt;

5-[4-[[3-Methyl-4-oxo-3,4-dihydro-(2H)-1,3-benzoxazine-2-yl]methoxy]phenyl methyl]thiazolidin-2,4-dione, sodium salt;

5-[4-[[1,3-Dimethyl-4-oxo-1,2,3,4-tetrahydro-2-quinazolinyl]methoxy]phenyl methylene]thiazolidin-2,4-dione;

5-[4-[[3-Methyl-4-oxo-1,2,3,4-tetrahydro-2-quinazolinyl]methoxy]phenyl methylene]thiazolidin-2,4,dione;

5-[4-[[1,3-Dimethyl-4-oxo-1,2,3,4-tetrahydro-2-quinazolinyl]methoxy]phenyl methyl]thiazolidin-2,4-dione;

5-[4-[[3-Methyl-4-oxo-1,2,3,4-tetrahydro-2-qunazolinyl]methoxy]phenyl methyl]thiazolidin-2,4-dione;

5-[4-[[3-Ethyl-1-methyl-4-oxo-1,2,3,4-tetrahydro-2-quinazolinyl]methoxy]phenyl methyl]thiazolidin-2,4-dione;

5-[4-[[1-Methyl-4-oxo-1,2,3,4-tetrahydro-2-quinazolinyl]methoxy]phenyl methyl]thiazolidin-2,4-dione;

5-[4-[[1,3-Dimethyl-4-oxo-1,2,3,4-tetrahydro-2-quinazolinyl]methoxy]phenyl methyl]thiazolidin-2,4-dione, sodium salt;

5-[4-[[4-Oxo-1,2,3,4-tetrahydro-2-quinazolinyl]methoxy]phenyl methyl]thiazolidin-2,4-dione;

5-[4-[[1,3-Diethyl-4-oxo-1,2,3,4-tetrahydro-2-quinazolinyl]methoxy]phenyl methyl]thiazolidin-2,4-dione;

5-[4-[[1-Ethyl-3-methyl-4-oxo-1,2,3,4-tetrahydro-2-quinazolinyl]methoxy]phenyl methyl]thiazolidin-2,4-dione; and 5-[4-[[1-Ethyl-4-oxo-1,2,3,4-tetrahydro-2-quinazolinyl]methoxy]phenyl methyl]thiazolidin-2,4-dione.

The invention also includes an intermediate of formula (III)

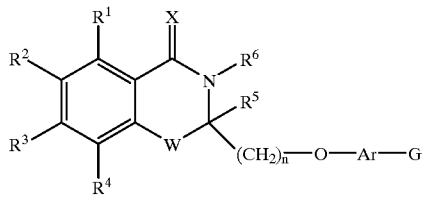

(III)

wherein X represents O or S; the groups $R^1$, $R^2$, $R^3$, $R^4$ may be same or different and represent hydrogen, halogen, hydroxy, cyano, nitro; optionally substituted groups selected from alkyl, cycloalkyl, alkoxy, cycloalkyloxy, aryl, aralkyl, heteroaryl, heteroaralkyl, heterocyclyl, aryloxy, alkoxycarbonyl, aryloxycarbonyl, aralkoxycarbonyl, alkylamino, arylamino, amino, aminoalkyl, hydroxyalkyl, alkoxyalkyl, thioalkyl, alkylthio, acyl, acylamino, aryloxycarbonylamino, aralkoxycarbonylamino, alkoxycarbonylamino, carboxylic acid or its derivatives, acyloxy, sulfonic acid or its derivatives; W represents O, S or a group $NR^9$; $R^6$ and $R^9$ may be same or different and represent hydrogen or optionally substituted alkyl, cycloalkyl, aryl, aralkyl, heterocyclyl, heteroaryl, heteroaralkyl, acyl, hydroxyalkyl, aminoalkyl, alkoxycarbonyl, aryloxycarbonyl, aralkoxycarbonyl, alkoxyalkyl, alkylthio, or thioalkyl groups; $R^5$ represents hydrogen, hydroxy or halogen or optionally substituted alkyl, aryl, heteroaryl, acyl, alkoxy, aralkyl, or aralkoxy; n is an integer ranging from 1–4; Ar represents an optionally substituted divalent aromatic or heterocyclic group; G represents CHO, $NO_2$, —$NH_2$ or —$CH_2CH(J)$—COOR, where J represents a halogen atom and R represents H or lower alkyl group.

According to a feature of the present invention, there is provided a process for the preparation of novel intermediate of the general formula (III)

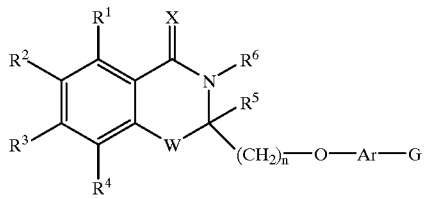

(III)

where $R^1$, $R^2$, $R^3$, $R^4$, $R^5$, $R^6$, X, W, n, and Ar are as defined earlier, G represents —CHO or —$NO_2$ group which comprises, reacting a compound of the general formula (IV)

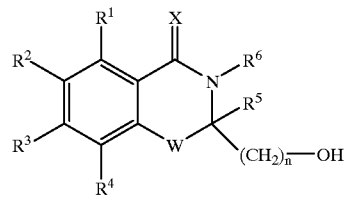

(IV)

wherein, $R^1$, $R^2$, $R^3$, $R^4$, $R^5$, $R^6$, X, W, and n are as defined earlier, with a compound of general formula (V)

$$L^1—Ar—G \quad (V)$$

where $L^1$ is a halogen atom such as fluorine or chlorine, G is a CHO or a $NO_2$ group and Ar is as defined earlier.

The reaction of a compound of formula (IV) with a compound of formula (V) to produce a compound of formula (III) may be carried out in the presence of solvents such as THF, DMF, DMSO, DME and the like or mixtures thereof. The inert atmosphere may be maintained by using inert gases such as $N_2$, Ar or He. The reaction may be effected in the presence of a base such as $K_2CO_3$, $Na_2CO_3$, NaH and the like. Mixture of bases may be used The reaction temperature may range from 20° C. to 150° C., preferably at a temperature in the range of 30° C. to 100° C. The duration of the reaction may range from 1 to 24 hours, preferably from 2 to 6 hours.

In another embodiment of the present invention, the novel intermediate of general formula (III), where G is a CHO or $NO_2$ group, can also be prepared by the reaction of compound of general formula (VI)

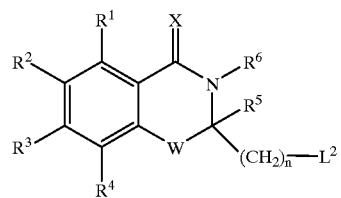

(VI)

where $R^1$, $R^2$, $R^3$, $R^4$, $R^5$, $R^6$, X, W, and n are as defined earlier and $L^2$ may be a halogen atom such as Cl, Br, I or a leaving group such as methanesulfonate, trifluoromethanesulfonate, p-toluenesulfonate with a compound of general formula (VII)

$$HO—Ar—G \quad (VII)$$

where G is a CHO or $NO_2$ group and Ar is as defined earlier.

The reaction of a compound of formula (VI) with a compound of formula (VII) to produce a compound of the formula (III) may be carried out in the presence of solvents such as THF, DMF, DMSO, DME and the like or mixtures thereof. The reaction may be carried out in an inert atmosphere which may be maintained by using inert gases such as $N_2$, Ar, or He. The reaction may be effected in the presence of a base such as $K_2CO_3$, $Na_2CO_3$ or NaH or mixtures thereof. The reaction temperature may range from 20° C.–120° C., preferably at a temperature in the range of 30° C.–100° C. The duration of the reaction may range from 1–12 hours, preferably from 2 to 6 hours.

Alternatively, a compound of general formula (III) can also be prepared by the reaction of compound of general formula (IV) defined earlier with a compound of general formula (VII) defined earlier.

The reaction of compound of general formula (IV) with a compound of general formula (VII) may be carried out using suitable coupling agents such as dicyclohexyl urea, triarylphosphine/dialkylazadicarboxylate such as $PPh_3$/DEAD and the like. The reaction may be carried out in the presence of solvents such as THF, DME, $CH_2Cl_2$, $CHCl_3$, toluene, acetonitrile, carbontetrachloride and the like. The inert atmosphere may be maintained by using inert gases such as $N_2$, Ar, and He. The reaction may be effected in the presence of DMAP, HOBT and they may be used in the range of 0.05 to 2 equivalents, preferably 0.25 to 1 equivalents. The reaction temperature may be in the range of 0° C. to 100° C., preferably at a temperature in the range of 20° C. to 80° C. The duration of the reaction may range from 0.5 to 24 hours, preferably from 6 to 12 hours.

The present invention provides a process for the preparation of novel azolidinedione derivatives of general formula (I), their tautomeric forms, their stereoisomers, their polymorphs, their pharmaceutically acceptable salts and their pharmaceutically acceptable solvates wherein $R^1$, $R^2$, $R^3$, $R^4$, $R^5$, $R^6$, X, W, n, Ar and B are as defined earlier and $R^7$ together with $R^8$ represent a bond which comprises:

reacting the novel intermediate of the general formula (III) obtained above where G represents CHO group with 2,4-thiazolidinedione or 2,4-oxazolidinedione and removing the water formed during the reaction by conventional methods to yield a compound of general formula (VIII)

(VIII)

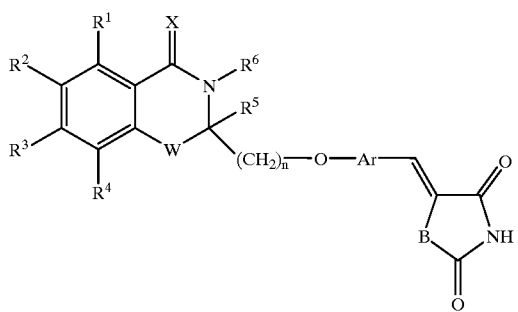

where $R^1$, $R^2$, $R^3$, $R^4$, $R^5$, $R^6$, X, W, n, and Ar are as defined earlier and B represents sulfur or oxygen. The compound of general formula (VIII) represents a compound of general formula (I), wherein $R^7$ and $R^8$ together represent a bond and all other symbols are as defined earlier.

The reaction of compound of the general formula (III) where G is a CHO group with 2,4-thiazolidinedione or 2,4-oxazolidinedione, to yield compound of general formula (VIII), may be carried out neat in the presence of sodium acetate or in the presence of a solvent such as benzene, toluene, methoxyethanol or mixtures thereof. The reaction temperature may range from 80° C. to 140° C. depending upon the solvents employed and in the range from 80° C. to 180° C. when the reaction is carried out neat in the presence of sodium acetate. Suitable catalyst such as piperidinium acetate or benzoate, sodium acetate or mixtures of catalysts may also be employed. Sodium acetate can be used in the presence of solvent, but it is preferred that sodium acetate is used neat. The water produced in the reaction may be removed, for example, by using Dean Stark water separator or by using water absorbing agents like molecular seives.

Oxazolidine-2-oxo-4-thione may be used instead of 2,4-oxazolidinedione, wherein the thio group may be converted to oxo group by oxidation using agents such as hydrogen peroxide or peroxyacids like mCPBA.

The compound of the general formula (VIII) obtained above is converted into its pharmaceutically acceptable salts, or its pharmaceutically acceptable solvates by conventional methods.

The compound of the general formula (VIII) obtained in the manner described above is reduced by known methods to obtain the compound of general formula (IX).

(IX)

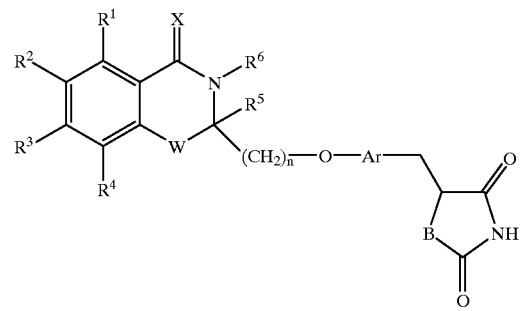

wherein $R^1$, $R^2$, $R^3$, $R^4$, $R^5$, $R^6$, X, W, n, Ar and B are as defined earlier. The compound of general formula (IX) represents a compound of general formula (I), wherein $R^7$ and $R^8$ represent hydrogen atoms and other symbols are as defined earlier.

The reduction of compound of the formula (VIII) to yield a compound of the general formula (IX) may be carried out in the presence of gaseous hydrogen and a catalyst such as Pd/C, Rh/C, Pt/C, Raney nickel, and the like. Mixtures of catalysts may be used. The reaction may also be conducted in the presence of solvents such as dioxane, acetic acid, ethyl acetate and the like or mixtures thereof. A pressure between atmospheric pressure 80 psi may be employed. The catalyst may be 5–10% Pd/C and the amount of catalyst used may range from 50–300% w/w. The reaction may also be carried out by employing metal solvent reduction such as magnesium in methanol or sodium amalgam in methanol. The reaction may also be carried out with alkali metal borohydrides such as $LiBH_4$, $NaBH_4$, $KBH_4$ and the like in the presence of cobalt salt such as $CoCl_2$ and ligands, preferably bidentated ligands such as 2, 2'-bipyridyl, 1, 10-phenanthroline, bisoximes and the like.

The compound of the general formula (IX) obtained above is converted into its pharmaceutically acceptable salts, or its pharmaceutically acceptable solvates by conventional methods.

In yet another embodiment of the present invention, the compound of the general formula (I) can also be prepared by reacting a compound of the general formula (VI) defined above with a compound of general formula (X)

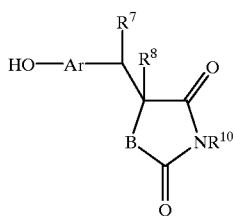

where $R^7$, $R^8$, B and Ar are as defined earlier and $R^{10}$ is hydrogen or a nitrogen protecting group which is removed after the reaction.

The reaction of compound of formula (VI) with compound of formula (X) to produce a compound of the formula (I) may be carried out in the presence of solvents such as THF, DMF, DMSO, DME and the like or mixtures thereof. The reaction may be carried out in an inert atmosphere which may be maintained by using inert gases such as $N_2$, Ar or He. The reaction may be effected in the presence of a base such as $K_2CO_3$, $Na_2CO_3$ or NaH or mixtures thereof. The reaction temperature may range from 20° C.–150° C., preferably at a temperature in the range of 30° C.–80° C. The duration of the reaction may range from 1–12 hours, preferably from 2 to 6 hours.

Alternatively, compound of the general formula (I) can also be prepared by reacting a compound of general formula (IV) defined earlier with a compound of general formula (X) defined above.

The reaction of compound of general formula (IV) with a compound of general formula (X) may be carried out using suitable coupling agents such as dicyclohexyl urea, triarylphosphine/dialkylazadicarboxylate such as $PPh_3$/DEAD and the like. The reaction may be carried out in the presence of solvents such as THF, DME, $CH_2Cl_2$, $CHCl_3$, toluene, acetonitrile, carbontetrachloride and the like. The inert atmosphere may be maintained by using inert gases such as $N_2$, Ar, He. The reaction may be effected in the presence of DMAP, HOBT and they may be used in the range of 0.05 to 2 equivalents, preferably 0.25 to 1 equivalents. The reaction temperature may be in the range of 0° C. to 100° C., preferably at a temperature in the range of 20° C. to 80° C. The duration of the reaction may range from 0.5 to 24 hours, preferably from 6 to 12 hours.

In another embodiment of the present invention, the compound of general formula (I), where $R^1$, $R^2$, $R^3$, $R^4$, $R^5$, $R^6$, X, W, n, and Ar are as defined earlier and $R^7$ and $R^8$ represent hydrogen atoms, B represents S can be prepared by the reaction of compound of general formula (XI)

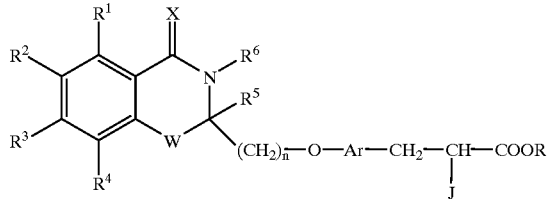

where $R^1$, $R^2$, $R^3$, $R^4$, $R^5$, $R^6$, X, W, n, and Ar are as defined earlier, J is a halogen atom like chlorine, bromine or iodine and R is a lower alkyl group with thiourea followed by treatment with an acid.

The reaction of compound of general formula (XI) with thiourea is normally carried out in the presence of alcoholic solvent such as methanol, ethanol, propanol, isobutanol, 2-methoxybutanol and the like or DMSO or sulfolane. The reaction may be conducted at a temperature in the range between 20° C. and the reflux temperature of the solvent used. Bases such as NaOAc, KOAc, NaOMe, NaOEt and the like may be used. The reaction is normally followed by treatment with a mineral acid such as hydrochloric acid at 20° C.–100° C.

The compound of general formula (XI) where all the symbols are as defined earlier can be prepared by the diazotization of the amino compound of the general formula (XII)

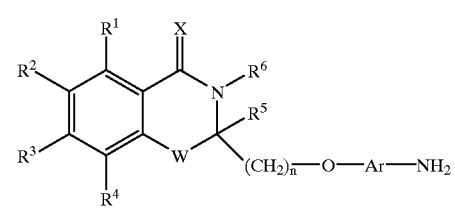

where all symbols are as defined earlier, using alkali metal nitrites followed by treatment with acrylic acid esters in the presence of hydrohalo acids and catalytic amount of copper oxide or copper halide.

The compound or general formula (XII) can in turn prepared by the conventional reduction of the novel intermediate (III) where G is $NO_2$ group and other symbols are as defined earlier.

In yet another embodiment of the present invention, the compound of general formula (I), can also be prepared by reacting the compound of general formula (XIII)

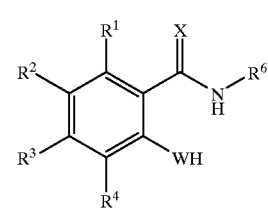

where $R^1$, $R^2$, $R^3$, $R^4$, $R^6$, X, and W are as defined earlier, with a compound of general formula (XIV)

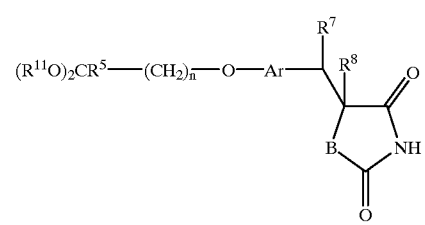

where Ar, $R^5$, $R^7$, $R^8$, B and n are as defined earlier, and $R^{11}$ may be a linear or branched ($C_1$–$C_5$) alkyl group such as methyl, ethyl, propyl, isopropyl, t-butyl and the like.

The reaction of compound of general formula (XIV) with compound of general formula (XIII) to produce a compound of general formula (I) may be carried out in neat or in the presence of solvents such as THF, CHCl$_3$, benzene, toluene, hexane, dioxane and the like or mixture thereof. The reaction may be carried out at a temperature in the range of 0° C. to 250° C. preferably at a temperature in the range of 10° C. to 150° C. The reaction may be carried out in the presence of an acid or a base. The selection of acid or base is not critical. The examples of such acids include H$_2$SO$_4$, HCl, pTsOH, PPE (polyphosphoric ethyl ester) and the like. Examples of bases include pyrrolidine, piperidine and the like. The reaction may be carried out in an inert atmosphere which may be maintained by using inert gases such as N$_2$, Ar or He. The duration of the reaction may range from 0.25 to 24 h preferably, from 1 to 12 h.

In another embodiment of the present invention, there is provided a process for the preparation of novel intermediate of general formula (XIV) as defined above, where all the symbols are as defined earlier which comprises, reacting a compound of the general formula (XV)

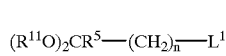
(XV)

where all symbols are as defined earlier with a compound of general formula (X) where R$^7$, R$^8$, B and Ar are as defined earlier and R$^{10}$ is hydrogen or a nitrogen protecting group which is removed after the reaction.

The reaction of compound of formula (XV) with compound of formula (X) to produce a compound of the formula (XIV) may be carried out in the presence of solvents such as THF, DMF, DMSO, DME and the like or mixtures thereof. The reaction may be carried out in an inert atmosphere which may be maintained by using inert gases such as N$_2$, Ar or He. The reaction may be effected in the presence of a base such as K$_2$CO$_3$, Na$_2$CO$_3$ or NaH or mixtures thereof. The reaction temperature may range from 20° C.–120° C., preferably at a temperature in the range of 30° C.–80° C. The duration of the reaction may range from 1–12 hours, preferably from 2 to 6 hours.

In still another embodiment of the present invention, the compound of general formula (XIV) where R$^7$ and R$^8$ represents hydrogen atom and all other symbols are as defined earlier can be prepared from the compound of general formula (XVI)

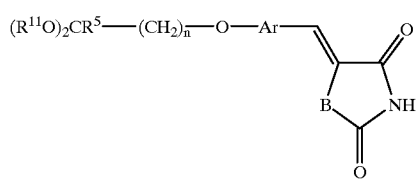
(XVI)

where all the symbols are as defined above, by reducing under known methods.

The reduction of compound of the formula (XVI) to yield a compound of the general formula (XIV) may be carried out in the presence of gaseous hydrogen and a catalyst such as Pd/C, Rh/C, Pt/C, and the like. Mixtures of catalysts may be used. The reaction may also be conducted in the presence of solvents such as dioxane, acetic acid, ethyl acetate and the like. A pressure between atmospheric pressure and 80 psi may be employed. The catalyst may be 5–10% Pd/C and the amount of catalyst used may range from 50–200% w/w. The reaction may also be carried out by employing metal solvent reduction such as magnesium in methanol or sodium amalgam in methanol.

The reaction may also be carried out with Raney Nickel in the presence of hydrogen gas or alkali metal borohydrides such as LiBH$_4$, NaBH$_4$, KBH$_4$ and the like in the presence of cobalt salt such as CoCl$_2$ and ligands, preferably bidentated ligands such as 2, 2'-bipyridyl, 1, 10-phenanthroline, bisoximes and the like.

The present invention also provides a process for the preparation of novel intermediate of general formula (XVI) where all the symbols are as defined earlier, which comprises reacting the intermediate (XVII)

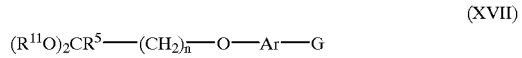
(XVII)

where G represents CHO group, and all the symbols are as defined earlier, with 2,4-thiazolidinedione or 2,4-oxazolidinedione and removing the water formed during the reaction by conventional methods.

The reaction between the compound of the general formula (XVII) where G is a CHO group with 2,4-thiazolidinedione or 2,4-oxazolidinedione, to yield compound of general formula (XVI) wherein B represents a sulfur or an oxygen atom respectively, may be carried out neat in the presence of sodium acetate or in the presence of a solvent such as benzene, toluene, methoxyethanol or mixtures thereof. The reaction temperature may range from 80° C. to 140° C. depending upon the solvents employed and in the range from 80° C. to 180° C. when the reaction is carried out neat in the presence of sodium acetate. Suitable catalyst such as piperidinium acetate or benzoate, sodium acetate or mixtures of catalysts may also be employed. Sodium acetate can be used in the presence of solvent, but it is preferred that sodium acetate is used neat. The water produced in the reaction may be removed, for example, by using Dean Stark water separator or by using water absorbing agents like molecular seives. Oxazolidine-2-oxo-4-thione may be used instead of 2,4-oxazolidinedione, wherein the thio group may be converted to oxo group by oxidation using agents such as hydrogen peroxide or peroxyacids like mCPBA.

The compound of formula (XVII) is in turn prepared by reacting a compound of formula (XV)

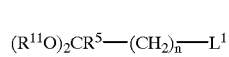
(XV)

where all symbols are as defined earlier and L$^1$ is a leaving group, with a compound of formula (VII)

(VII)

where G is a CHO group and Ar is as defined earlier.

The reaction of a compound of formula (XV) with a compound of formula (VII) to produce a compound of the formula (XVII) may be carried out in the presence of solvents such as THF, DMF, DMSO, DME and the like or mixtures thereof. The reaction may be carried out in an inert atmosphere which may be maintained by using inert gases such as N$_2$, Ar, or He. The reaction may be effected in the presence of a base such as K$_2$CO$_3$, Na$_2$CO$_3$ or NaH or mixtures thereof. The reaction temperature may range from 20° C.–120° C., preferably at a temperature in the range of 30° C.–100° C. The duration of the reaction may range from 1–12 hours, preferably from 2 to 6 hours.

In another embodiment of the present invention the compound of formula (I) where $R^7$ and $R^8$ together represent a bond and all other symbols are as defined earlier may be prepared by reacting a compound of general formula (XVI) with a compound of general formula (XIII) using similar conditions as that followed for the reaction of compound of formula (XIII) with a compound of formula (XIV) as described earlier.

In yet another embodiment of the present invention, the compound of general formula (I) where $R^5$ is hydrogen atom, W represents NH and all other symbols are as defined earlier can also be prepared by reducing the compound of general formula (XVIII) (disclosed in copending U.S. application Ser. Nos. 08/777,627 and 08/884,816).

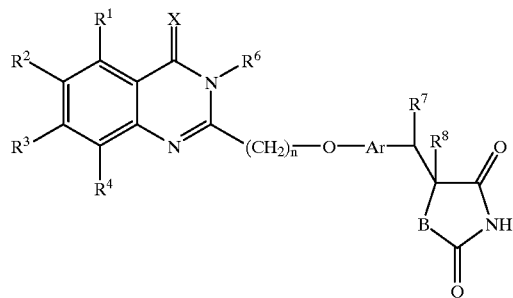

(XVIII)

where $R^7$ and $R^8$ represents hydrogen atom or together form a bond and all other symbols are as defined earlier.

The reduction of compound of the formula (XVIII) to yield a compound of the general formula (I) may be carried out in the presence of gaseous hydrogen and a catalyst such as Pd/C, Rh/C, Pt/C and the like. Mixture of catalysts may be used. The reaction may also be carried out in the presence of solvents such as dioxane, acetic acid, ethyl acetate and the like. A pressure between atmospheric pressure and 80 psi may be employed. The catalyst may be 5–10% Pd/C and the amount of catalyst used may range from 30–50 w/w. The duration of the reaction may range from 12 to 24 h and the temperature of the reaction may range from 25° C. to 80° C.

The compound of general formula (VI) defined earlier may be prepared from compound of general formula (IV) defined earlier using conventional organic transformations that one skilled in the art would use.

The compound of general formula (VI) and of general formula (IV) defined earlier may be prepared by the reaction of compound of general formula (XIII) defined earlier with a compound of formula (XIX)

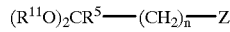

(XIX)

where $R^{11}$, $R^5$ and n are as defined earlier and Z represents hydroxy or a leaving group $L^1$ such as chloride, bromide, p-toluenesulfonate, methanesulfonate, trifluoromethanesulfonate and the like.

The reaction of compound of (XIII) with a compound of formula (XIX) to yield a compound of formula (VI) or (IV) may be carried out using similar conditions described for the reaction of formula (XIII) with the compound of general formula (XIV).

The pharmaceutically acceptable salts are prepared by reacting the compound of formula (I) with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixture of solvents may be used. Organic bases like lysine, arginine, diethanolamine, choline, guanidine and their derivatives etc. may also be used. Alternatively, acid addition salts are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid, salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

The term neat as used in this application means the reaction is carried out without the use of a solvent.

The stereoisomers of the compounds forming part of this invention may be prepared by using reactants in their single enantiomeric form in the process wherever possible or by conducting the reaction in the presence of reagents or catalysts in their single enantiomeric form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid and the like or chiral bases such as brucine, cinchona alkaloids and their derivatives and the like.

Various polymorphs of compound of general formula (I) forming part of this invention may be prepared by crystallization of compound of formula (I) under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe nmr spectroscopy, ir spectroscopy, differential scanning calorimetry, powder X-ray diffraction or such other techniques.

The present invention also provides a pharmaceutical composition, containing the compounds of the general formula (I), as defined above, their tautomeric forms, their stereoisomers, their polymorphs, their pharmaceutically acceptable salts, their pharmaceutically acceptable solvates or mixtures thereof in combination with the usual pharmaceutically employed carriers, diluents and the like, useful for the treatment and/or prophylaxis of hyperlipidemia, hypercholesterolemia, hyperglycemia, osteoporosis, obesity, glucose intolerance, insulin resistance and also diseases or conditions in which insulin resistance is the underlying pathophysiological mechanism such as type II diabetes, impaired glucose tolerance, dyslipidaemia, hypertension, coronary heart disease and other cardiovascular disorders including atherosclerosis; insulin resistance associated with obesity and psoriasis, for treating diabetic complications and other diseases such as polycystic ovarian syndrome (PCOS), certain renal diseases including diabetic nephropathy, glomerulonephritis, glomerular sclerosis, nephrotic syndrome, hypertensive nephrosclerosis, end-stage renal diseases and microalbuminuria as well as certain eating disorders, as aldose reductase inhibitors and for improving cognitive functions in dementia.

The pharmaceutical composition may be in the forms normally employed, such as tablets, capsules, powders, syrups, solutions, suspensions and the like, may contain flavourants, sweeteners etc. in suitable solid or liquid carriers or diluents, or in suitable sterile media to form injectable solutions or suspensions. Such compositions typically contain from 1 to 20%, preferably 1 to 10% by weight of active compound, the remainder of the composition being pharmaceutically acceptable carriers, diluents, excipients, or solvents.

A typical tablet production method is exemplified below:
Tablet Production Example

| a) 1) Active ingredient | 10 g |
|---|---|
| 2) Lactose | 110 g |
| 3) Corn starch | 35 g |
| 4) Carboxymethyl cellulose | 44 g |
| 5) Magnesium stearate | 1 g |
| | 200 g for 1000 tablets |

The ingredients 1 to 3 are uniformly blended with water and granulated after drying under reduced pressure. The ingredient 4 and 5 are mixed well with the granules and compressed by tabletting machine to prepare 1000 tablets each containing 10 mg of active ingredient.

| b) 1) Active ingredient | 10 g |
|---|---|
| 2) Calcium phosphate | 90 g |
| 3) Lactose | 50 g |
| 4) Corn starch | 45 g |
| 5) Polyvinyl pyrrolidone | 3.5 g |
| 6) Magnesium stearate | 15 g |
| | 200 g for 1000 tablets |

The ingredients 1 to 4 are uniformly moistened with an aqueous solution of ingredient 5 and granulated after drying under reduced pressure. Ingredient 6 is added and granules are compressed by a tabletting machine to prepare 1000 tablets containing 10 mg of active ingredient 1.

The compound of the formula (I) as defined above are clinically administered to mammals, including man, via either oral or parenteral routes. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.10 mg to about 200 mg/kg body weight of the subject per day or preferably about 0.10 mg to about 30 mg/kg body weight per day administered singly or as a divided dose. However, the optimum dosage for the individual subject being treated will be determined by the person responsible for treatment, generally smaller doses being administered initially and thereafter increments made to determine the most suitable dosage.

Suitable pharmaceutically acceptable carriers include solid fillers or diluents and sterile aqueous or organic solutions. The active compound will be present in such pharmaceutical compositions in the amounts sufficient to provide the desired dosage in the range as described above. Thus, for oral administration, the compounds can be combined with a suitable solid or liquid carrier or diluent to form capsules, tablets, powders, syrups, solutions, suspensions and the like. The pharmaceutical compositions, may, if desired, contain additional components such as flavourants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or salts with base of the compounds. The injectable solutions prepared in this manner can then be administered intravenously, intraperitoneally, subcutaneously, or intramuscularly, with intramuscular administration being preferred in humans.

The invention is explained in detail in the examples given below which are provided by way of illustration only and therefore should not be construed to limit the scope of the invention.

Preparation 1

4-[[2-Methyl-4-oxo-3,4-dihydro-(2H)-1,3-benzoxazine-2-yl] methoxy]nitrobenzene:

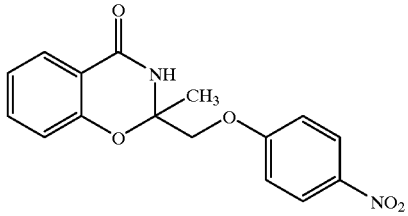

Step A: Preparation of 4-[2-oxo-propoxy]nitrobenzene

To stirred suspension of $K_2CO_3$ (50.0 g, 0.36 mol) in dry DMF (500 mL) was added 4-nitrophenol (25.0 g, 0.18 mol) and stirred for 30 min at 25° C. Chloroacetone (21.5 mL, 0.27 mol) was added to the reaction mixture and stirred for 24 h at 25–30° C. The reaction mixture was filtered through a buchner funnel. The filtrate was poured into water (500 mL) and extracted with ethyl acetate (3×300 mL). The combined organic layers were washed with brine, dried over anhydrous $Na_2SO_4$ and concentrated. The crude compound was purified by column chromatography using EtOAc: Pet. ether (1:2) as eluent to yield the title compound (11.0 g, 31%) as a colourless liquid.

$^1$H NMR (CDCl$_3$): δ8.22 (d, J=9.17 Hz, 2H), 6.95 (d, J=9.17 Hz, 2H), 4.67 (s, 2H), 2.30 (s, 3H).

Step B

To a stirred mixture of salicylamide (6.85 g, 50 mmol) and 4-[2-oxo-propyloxy]nitrobenzene (9.75 g, 50 mmol) in benzene (500 mL) was added piperidine (0.52 mL, 5 mmol). The reaction mixture was immersed in a pre-heated oil bath (~100° C.) and refluxed for 10 h with continuous removal of water using Dean-Stark water separator. The reaction mixture was cooled to room temperature and the precipitated brown coloured solid was filtered, washed with benzene and dried to afford the title compound (13.5 g, 86%).

$^1$H NMR (CDCl$_3$): δ8.76 (bs, 1H, D$_2$O exchangeable), 8.14 (d, J=9.20 Hz, 2H), 7.82 (d, j=7.50 Hz, 1H), 7.42 (t, J=7.50 Hz, 1H), 7.06 (t, J=7.50 Hz, 1H), 6.99 (d, J=9.20 Hz, 2H), 6.88 (d, j=7.50 Hz, 1H), 4.30 (d, J=10.33 Hz, 1H), 4.14 (d, J=10.33 Hz, 1H), 1.72 (s, 3H).

Preparation 2

4-[[2,3-Dimethyl-4-oxo-3,4-dihydro-(2H)-1,3-benzoxazine-2-yl]methoxy]nitrobenzene:

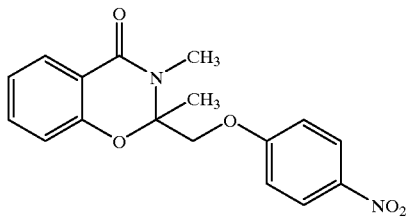

To a stirred mixture of 4-[[2-methyl-4-oxo-3,4-dihydro-(2H)-1,3-benzoxazine-2-yl]methoxy]nitrobenzene (5.0 g, 15.9 mmol) obtained in preparation 1 and $K_2CO_3$ (6.6 g, 47.7 mmol) in acetone (60 mL) was added $CH_3I$ (9.9 mL, 159 mmol) and refluxed for 12 h. The reaction mixture was cooled to room temperature, filtered through buchner funnel to remove all the inorganic salts and acetone was removed at 40° C. The residue was poured into water (50 mL) and extracted with ethyl acetate (3×50 mL). The organic extracts were washed with brine, dried over anhydrous $Na_2SO_4$ and concentrated to afford the title compound (5.1 g, 98%).

$^1$H NMR (CDCl$_3$): δ8.19 (d, J=9.10 Hz, 2H), 7.94 (d, J=7.50 Hz, 1H), 7.42 (t, J=7.50 Hz, 1H), 7.11 (t, J=7.50 Hz, 1H), 6.95 (d, J=9.10 Hz, 2H), 6.88 (d, J=7.50 Hz, 1H), 4.30–4.10 (m, 2H), 3.22 (s, 3H), 1.88 (s, 3H).

Preparation 3

4-[[2,3-Dimethyl-4-oxo-3,4-dihydro-(2H)-1,3-benzoxazine-2-yl]methoxy]aniline:

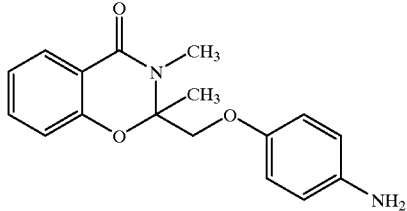

A solution of 4-[[2,3-dimethyl-4-oxo-3,4-dihydro-(2H)-1,3-benzoxazine-2-yl]methoxy] nitrobenzene (5.0 g, 15.2 mmol) obtained in preparation 2, in 1,4-dioxane (100 mL) was reduced with hydrogen in the presence of 10% palladium charcoal (500 mg) at 40 psi for 16 h. The reaction mixture was filtered through a bed of celite and washed with dioxane and evaporated to dryness under reduced pressure to yield the title compound (4.2 g, 93%), mp: 162–164° C. $^1$H NMR (CDCl$_3$): δ7.92 (d, J=7.35 Hz, 1H), 7.40 (t, J=7.35 Hz, 1H), 7.05 (t, J=7.35 Hz, 1H), 6.87 (d, J=7.35 Hz, 1H), 6.68–6.52 (m, 4H), 4.12–3.98 (m, 2H), 3.18 (s, 3H), 1.8 (s, 3H).

Preparation 4

Ethyl 2-bromo-3-[4-[[2,3-dimethyl-4-oxo-3,4-dihydro-(2H)-1,3-benzoxazine-2-yl]methoxy]phenyl]propionate:

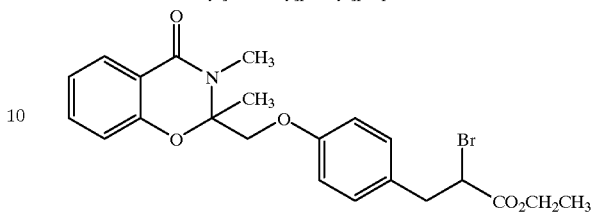

To a stirred solution of 4-[[2,3-dimethyl-4-oxo-3,4-dihydro-(2H)-1,3-benzoxazine-2-yl]methoxy]aniline (2.5 g, 8.4 mmol) obtained from preparation 3, in acetone (20 mL) was added aq HBr (6 mL, 33.6 mmol, 47%) and stirred for 20 min at 0–10° C. A solution of $NaNO_2$ (638 mg, 9.24 mmol) in water (1.5 mL) was added slowly dropwise at 0–10° C. and stirred further for 30 min at 0–15° C. To the reaction mixture, ethyl acrylate (5.5 mL, 50.4 mmol) was added and allowed to warm to 30° C. Catalytic amount of cuprous oxide (200 mg) was added in one portion and the reaction mixture was stirred further for 1 h at 30° C. Acetone was removed under reduced pressure. The resultant residue was extracted with ethyl acetate (3×25 mL). The combined organic layers were washed with ethyl acetate (3×25 mL), dilute $NH_3$ solution, water, followed by brine, dried over anhydrous $Na_2SO_4$. The solvent was evaporated under reduced pressure and the residue was purified by flash chromatography using EtOAc: pet. ether (4:6) as an eluent to yield the title compound (1.5 g, 39%).

$^1$H NMR (CDCl$_3$): δ7.95 (d, J=7.50 Hz, 1H), 7.41 (t, J=7.50 Hz, 1H), 7.09 (d, J=8.30 Hz, 2H), 7.05 (d, J=7.50 Hz, 1H), 6.85 (d, J=7.50 Hz, 1H), 6.71 (d, J=8.30 Hz, 2H), 4.29 (dd, J=8.50, 7.05 Hz, 1H), 4.23–4.02 (m, 4H), 3.38 (dd, J=13.70, 7.05 Hz, 1H), 3.20 (s, 3H), 3.15 (dd, J=13.70, 8.50 Hz, 1H), 1.88 (s, 3H), 1.22 (t, J=7.30 Hz, 3H).

Preparation 5

4-[(2,2-diethoxy)ethoxy]benzaldehyde:

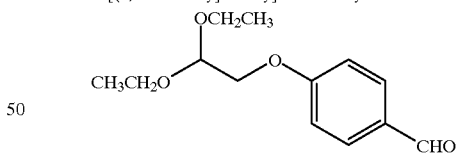

To a stirred suspension of sodium hydride (2.5 g, 100 mmol, 98%) in DMF (100 mL) was added a solution of 4-hydroxy benzaldehyde (10.0 g, 82 mmol) in DMF (100 mL) slowly dropwise at 25–30° C. and stirred for 30 min at 25–30° C. 2,2-diethoxy-1-bromoethane (19.7 g, 100 mmol) was added to the reaction mixture. The reaction mixture was immersed in a preheated oil bath at 60° C. and stirring was continued for 48 h at 60° C. The reaction mixture was cooled to room temperature, quenched with water (200 mL) and extracted with ethyl acetate (3×300 mL). The combined organic layers were washed with brine, dried over anhydrous $Na_2SO_4$ and concentrated. The crude compound was purified by column chromatography using EtOAc: pet. ether (1:2) as eluent to yield the title compound (12.65 g, 58%) as a brown coloured liquid.

$^1$H NMR (CDCl$_3$): δ9.88 (s, 1H), 7.82 (d, J=8.63 Hz, 2H), 7.02 (d, J=8.63 Hz, 2H), 4.85 (t, J=5.17 Hz, 1H), 4.08 (d, J=7.17 Hz, 2H), 3.88–3.50 (m, 4H), 1.24 (t, J=7.03 Hz, 6H).

EXAMPLE 1

5-[4-[(2,2-Diethoxy)ethoxy]phenylmethylene]thiazolidin-2,4-dione

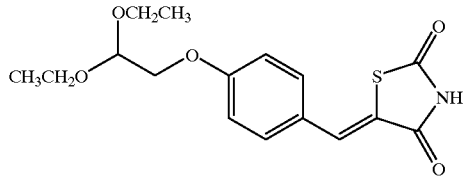

A mixture of 4-[(2,2-diethoxy)ethoxy]benzaldehyde (10.6 g, 44.53 mmol), thiazolidin-2,4-dione (5.21 g, 44.53 mmol), benzoic acid (0.70 g, 5.78 mmol) and piperidine (0.64 mL, 6.7 mmol) in toluene (150 mL) was refluxed for 2 h with continuous removal of water. The reaction mixture was cooled to room temperature and diluted with EtOAc (150 ml). The mixture was washed with water, brine, dried over anhydrous Na$_2$SO$_4$ and concentrated. The crude compound was purified by column chromatography using EtOAc: pet. ether (1:2) as eluent to afford the title compound (12.54 g, 70%) as a brown coloured liquid.

$^1$H NMR (CDCl$_3$): δ8.70 (bs, 1H, D$_2$O exchangeable), 7.80 (s, 1H), 7.45 (d, J=8.72 Hz, 2H), 7.02 (d, J=8.72 Hz, 2H), 4.87 (t, J=5.21 Hz, 1H), 4.08 (d, J=5.21 Hz, 2H), 3.90–3.52 (m, 4H), 1.26 (t, J=7.02 Hz, 6H).

EXAMPLE 2

5-[4-[(2,2-Diethoxy)ethoxy]phenylmethyl]thiazolidin-2,4-dione:

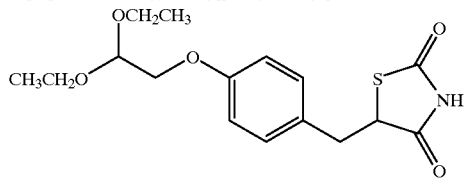

A solution of 5-[4-[(2,2-diethoxy)ethoxy]phenyl methylene]thiazolidin-2,4-dione (8.0 g, 23.7 mmol) obtained in example 1, in 1,4-dioxane (100 mL) was reduced with hydrogen in the presence of 10% palladium on charcoal (16.0 g) at 60 psi for 60 h. The mixture was filtered through a bed of celite. The filtrate was evaporated to dryness under reduced pressure; purified by column chromatography using EtOAc: pet. ether (1:1) as an eluent to afford the title compound (8.04 g, 67%) as a colourless liquid.

$^1$H NMR (CDCl$_3$): δ8.75 (bs, 1H, D$_2$O exchangeable), 7.14 (d, J=8.63 Hz, 2H), 6.87 (d, J=8.63 Hz, 2H), 4.84 (t, J=5.25 Hz, 1H), 4.49 (dd, J=9.46, 3.83 Hz, 1H), 3.99 (d, J=5.25 Hz, 2H), 3.88–3.52 (m, 4H), 3.45 (dd, J=14.11, 3.83 Hz, 1H), 3.10 (dd, J=14.11, 9.46 Hz, 1H), 1.25 (t, J=7.03 Hz, 6H).

EXAMPLE 3

5-[4-[[4-Oxo-3,4-dihydro-(2H)-1,3-benzoxazine-2-yl]methoxy]phenylmethyl]thiazolidin-2,4-dione:

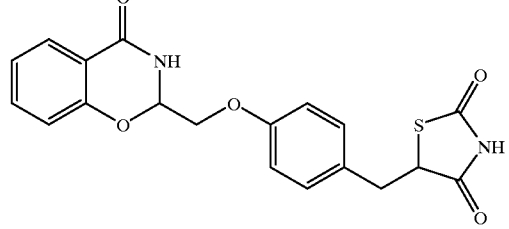

To a stirred solution of polyphosphonate ethyl ester (PPE) (3.15 g, 7.29 mmol) in chloroform (4.0 mL) was added salicylamide (0.5 g, 3.65 mmol) followed by addition of a solution of 5-[4-[(2,2-diethoxy)ethoxy]phenyl methyl]thiazolidin-2,4-dione (1.36 g, 4.0 mmol) obtained in example 2, in chloroform (10 mL) dropwise at 25–30° C. The reaction mixture was immersed in a preheated oil bath and refluxed for 3 h. The reaction mixture was cooled to room temperature and CHCl$_3$ was removed under reduced pressure. To the resultant residue aq. sat. NaHCO$_3$ solution (25 mL) was added and stirred for 30 min. at 25–30° C. The precipitated brown coloured solid was filtered and purified by column chromatography EtOAc: pet. ether (1:1) to yield the title compound (1.15 g, 81%). mp: 134° C.–138° C.

$^1$H NMR (CDCl$_3$): δ11.80 (bs, 1H, D$_2$O exchangeble), 8.40 (bs, 1H, D$_2$O exchangeable), 7.9 (d, J=7.50 Hz, 1H), 7.15 (d, J=8.30 Hz, 2H), 7.05 (t, J=7.50 Hz, 1H), 6.90 (d, J=7.50 Hz, 1H), 6.80 (d, J=8.30 Hz, 2H), 5.80 (t, J=5.30 Hz, 1H), 4.42 (dd, J=9.50, 3.80 Hz, 1H), 4.30–4.10 (m, 2H), 3.34 (dd, J=14.10, 3.80 Hz, 1H), 3.02 (dd, J=14.10, 9.50 Hz, 1H).

EXAMPLE 4

5-[4-[[3-Methyl-4-oxo-3,4-dihydro-(2H)-1,3-benzoxazine-2-yl]methoxy]phenylmethyl]thiazolidin-2,4-dione:

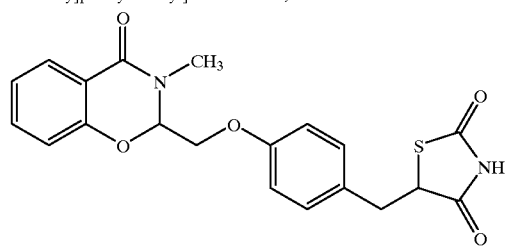

The title compound (0.4 g, 60%) was obtained from N-methyl salicylamide (250 mg, 1.66 mmol), 5-[4-[(2,2-diethoxy)ethoxy]phenyl methyl]thiazolidin-2,4-dione (620 mg, 1.82 mmol) obtained in example 2 and PPE (1.40 g, 3.32 mmol), by a similar procedure to that described in example 3. mp: 187° C.

$^1$H NMR (CDCl$_3$): δ8.23 (bs, 1H, D$_2$O, exchangeable), 7.95 (d, J=7.50 Hz, 1H), 7.43 (t, J=7.50 Hz, 1H), 7.12 (d, J=8.54 Hz, 2H), 7.08 (t, J=7.50 Hz, 1H), 6.93 (d, J=7.50 Hz, 1H), 6.77 (d, J=8.54 Hz, 2H), 5.62 (t, J=5.39 Hz, 1H), 4.48 (dd, J=9.04, 3.74 Hz, 1H), 4.32–4.08 (m, 2H), 3.45 (dd, J=14.05, 3.74 Hz, 1H), 3.21 (d, J=3.83 Hz, 3H), 3.10 (dd, J=14.05, 9.04 Hz, 1H).

EXAMPLE 5

5-[4-[[3-Ethyl-4-oxo-3,4-dihydro-(2H)-1,3-benzoxazine-2-yl]methoxy]phenylmethyl]thiazolidin-2,4-dione:

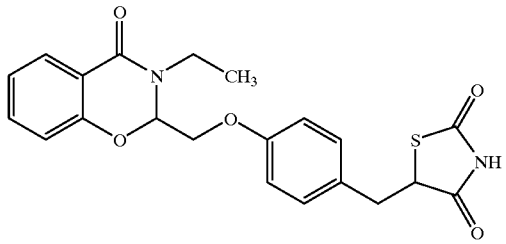

The title compound (0.51 g, 69%) was obtained from N-ethyl salicylamide (300 mg, 1.82 mmol) and 5-[4-[(2,2-diethoxy)ethoxy]phenyl methyl]thiazolidin-2,4-dione (677 mg, 1.99 mmol) obtained in example 2 and PPE (1.57 g, 3.64 mmol) by a similar procedure to that described in example 3. mp: 70–72° C.

$^1$H NMR (CDCl$_3$): δ8.10 (bs, 1H, D$_2$O exchangeable), 7.96 (d, J=7.50 Hz, 1H), 7.41 (t, J=7.50 Hz, 1H), 7.11 (d, J=8.40 Hz, 2H), 7.05 (t, J 7.50 Hz, 1H), 6.91 (d, J=7.50 Hz, 1H), 6.72 (d, J=8.40 Hz, 2H), 5.62 (t, J=5.40 Hz, 1H), 4.48 (dd, J=9.03, 3.87 Hz, 1H), 4.42–3.90 m, 3H), 3.50–3.02 (m, 3H), 1.28 (t, J=7.05 Hz, 3H).

EXAMPLE 6

Step A

5-[4-[[2,3-Dimethyl-4-oxo-3,4-dihydro-(2H)-1,3-benzoxazin-2-yl]methoxy]phenylmethyl]-2-iminothiazolidin-4-one:

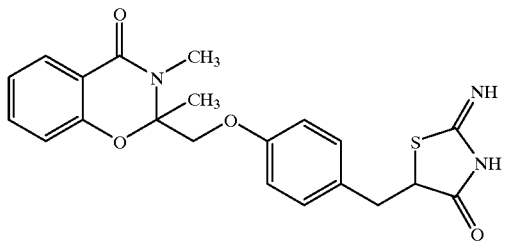

A mixture of ethyl 2-bromo-3-[4-[[2,3-dimethyl4-oxo-3,4-dihydro-(2H)-1,3-benzoxazine -2-yl]methoxy]phenyl] propionate (1.5 g, 3.25 mmol) obtained in preparation 4, fused sodium acetate (884 mg, 6.5 mmol) and thiourea (493 mg, 6.5 mmol) in ethanol (12 mL) was refluxed for 12 h. The reaction mixture was cooled to room temperature and ethanol was removed under reduced pressure. The resultant residue was diluted with ethyl acetate and washed with water. Ethyl acetate layer was dried over anhydrous Na$_2$SO$_4$ and concentrated. The crude compound was chromatographed on silica gel using EtOAc: pet. ether (1:1) as eluent to obtain the title compound (1.1 g, 82%).

$^1$H NMR (DMSO-d$_6$): δ7.91 (d, J=7.50 Hz, 1H), 7.40 (t, J=7.50 Hz, 1H), 7.05 (d, J=8.30 Hz, 2H), 7.02 (t, J=7.50 Hz, 1H), 6.88 (d, J=7.50 Hz, 1H), 6.70 (d, J=8.30 Hz, 2H), 4.41 (d, J=9.50, 3.75 Hz, 1H), 4.11 (s, 2H), 3.45 (dd, J=14.12, 3.75 Hz, 1H), 3.18 (s, 3H), 2.92 (dd, J=14.12, 9.50 Hz, 1H), 1.82 (s, 3H).

Step B

5-[4-[2,3-Dimethyl-4-oxo-3,4-dihydro-(2H)-1,3-benzoxazine-2-yl]methoxy]phenylmethyl]thiazolidin-2,4-dione:

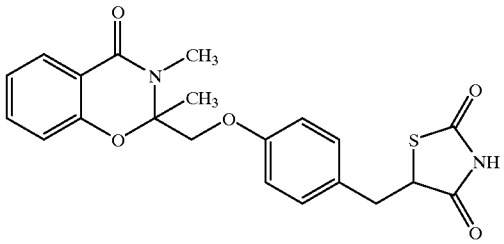

To a stirred solution of the compound (1 g, 2.43 mmol) obtained above in ethanol (20 mL) was added 2N HCl (5 mL) and refluxed for 12 h. The reaction mixture was cooled to room temperature and ethanol was removed under reduced pressure. The aqueous layer was neutralised with saturated aqueous NaHCO$_3$ solution and extracted with EtOAc (2×50 mL). The combined organic layers were washed with brine, dried over anhydrous Na$_2$SO$_4$ and concentrated. The crude compound was chromatographed on silica gel using EtOAc: pet. ether (1:1) as eluent to yield the title compound (450 mg, 45%). mp: 58–60° C.

$^1$H NMR (CDCl$_3$): δ7.92 (d, J=8.30 Hz, 1H), 7.42 (t, J=8.30 Hz, 1H), 7.12 (d, J=8.50 Hz, 2H), 7.06 (t, J=8.30 Hz, 1H), 6.87 (d, J=8.30 Hz, 1H), 6.76 (d, J=8.50 Hz, 2H), 4.50 (s, 2H), 4.48 (dd, J=9.30, 3.90 Hz, 1H), 3.40 (dd, J=14.11, 3.90 Hz, 1H), 3.18 (d, J=4.24 Hz, 3H), 3.08 (dd, J=14.11, 8.30 Hz, 1H), 1.85 (s, 3H).

EXAMPLE 7

5-[4-[[4-Oxo-3,4-dihydro-(2H)-1,3-benzoxazine-2-yl]methoxy] phenyl methyl]thiazolidin-2,4-dione, sodium Salt:

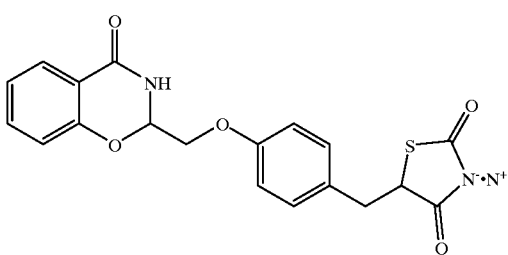

To a stirred suspension of 5-[4-[[4-oxo-3,4-dihydro-(2H)-1,3-benzoxazine-2-yl]methoxy]phenyl methyl]thiazolidin-2,4-dione (250 mg, 0.65 mmol) obtained from example 3, in methanol (4 mL) was added a solution of sodium methoxide (55 mg, 1.0 mmol) in methanol (1 mL) dropwise at 25–30° C. During this period the suspension slowly dissolved completely and a white solid precipitated out which was stirred further for 1 h. The solid was filtered and washed with methanol (2 mL) and dried to afford the title compound (250 mg, 95%). mp: 280° C.

$^1$H NMR (DMSO-d$_6$): δ7.70 (d, J=7.50 Hz, 1H), 7.35 (t, J=7.50 Hz, 1H), 7.10 (d, J=8.30 Hz, 2H), 7.00 (d, J=7.50 Hz, 1H), 6.85 (d, J=7.50 Hz, 1H), 6.75 (d, J=8.30 Hz, 2H), 5.70 (t, J=5.30 Hz, 1H), 4.05 (dd, J=8.95, 3.90 Hz, 1H), 3.90–3.80 (m, 2H), 3.23 (dd, J=13.80, 3.90 Hz, 1H), 2.65 (dd, J=13.80, 8.95 Hz, 1H).

EXAMPLE 8

5-[4-[[3-Methyl-4-oxo-3,4-dihydro-(2H)-1,3-benzoxazine-2-yl]methoxy]phenyl methyl]thiazolidin-2,4-dione, sodium salt:

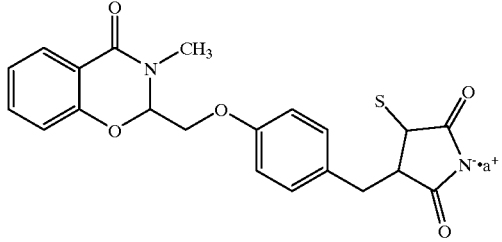

The title compound (136 mg, 81%) was obtained from 5-[4-[[3-methyl-4-oxo-3,4-dihydro -(2H 1,3-benzoxazine-2-yl]methoxy]phenyl methyl]thiazolidin-2,4-dione (150 mg, 0.39 mmol) obtained in example 4, by a similar procedure to that described in example 7. mp: 205–298° C.

$^1$H NMR (CDCl$_3$+DMSO-d$_6$): δ7.78 (d, J=7.50 Hz, 1H), 7.48 (t, J=7.50 Hz, 1H), 7.35–6.95 (m, 4H), 6.75 (d, J=8.30 Hz, 2H), 5.86 (t, J=4.98 Hz, 1H), 4.20 (d, J=4.98 Hz, 2H), 4.06 (dd, J=10.38, 3.23 Hz, 1H), 3.24 (dd, J=13.70, 3.23 Hz, 1H), 3.09 (s, 3H), 2.64 (dd, J=13.70, 10.38 Hz, 1H).

EXAMPLE 9

5-[4-[[1,3-Dimethyl-4-oxo-1,2,3,4-tetrahydro-2-quinazolinyl]methoxy] phenyl methylene]thiazolidin-2,4-dione:

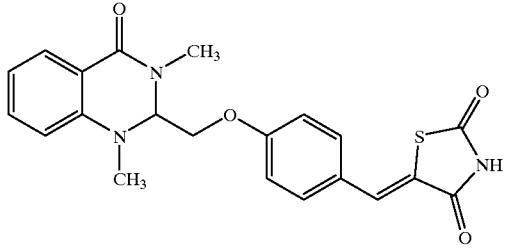

The title compound was obtained from N,N'-dimethylanthranilamide (500 mg, 3.04 mmol), 5-[4-[(2,2-diethoxy)ethoxy]phenyl methylene]thiazolidin-2,4-dione (1.13 g, 3.35 mmol) obtained in example 1 and PPE (2.63 g, 6.10 mmol) by a similar procedure to that described in example 3. mp: 236–240° C.

$^1$H NMR (DMSO-d$_6$): δ7.72 (d, J=7.47 Hz, 1H), 7.57 (s, 1H), 7.50–7.30 (m, 3H), 6.96 (d, J=8.30 Hz, 2H), 6.90–6.60 (m, 2H), 5.23 (t, J=5.30 Hz, 1H), 4.22 (d, J=5.30 Hz, 2H), 3.14 (s, 3H), 3.07 (s, 3H).

EXAMPLE 10

5-[4-[[3-Methyl-4-oxo-1,2,3,4-tetrahydro-2-quinazolinyl] methoxy] phenyl methylene]thiazolidin-2,4-dione:

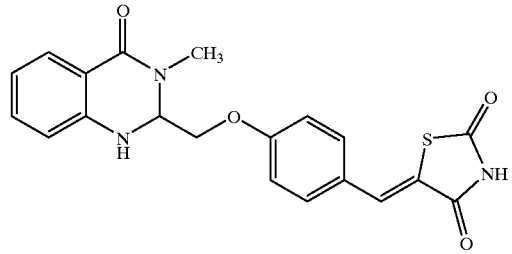

The title compound (800 mg, 65%) was obtained from N-methyl anthranilamide (500 mg, 3.3 mmol), 5-[4-[(2,2-diethoxy)ethoxy]phenyl methylene]thiazolidin-2,4-dione (1.23 g, 3.66 mmol) obtained from example 2 and PPE (2.85 g, 6.6 mmol) by a similar procedure to that described in example 3. mp: 66–68° C.

$^1$H NMR (DMSO-d$_6$): δ7.67 (s, 1H), 7.63 (d, J=7.80 Hz, 1H), 7.51 (d, J=8.60 Hz, 2H), 7.23 (t, J=7.80 Hz, 1H), 7.03 (d, J=8.60 Hz, 2H), 6.80–6.60 (m, 2H), 5.12 (t, J=5.30 Hz, 1H), 4.14 (d, J=5.30 Hz, 2H), 3.08 (s, 3H).

EXAMPLE 11

5-[4-[[1,3-Dimethyl-4-oxo-1,2,3,4-tetrahydro-2-quinazolinyl]methoxy] phenyl methyl]thiazolidin-2,4-dione:

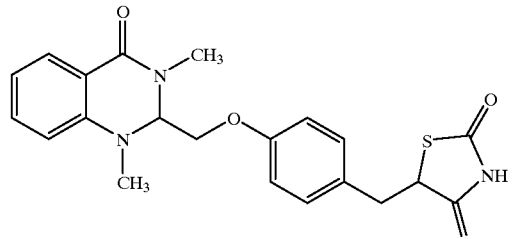

Method A

The title compound (3.84 g, 82%) was obtained from N,N'-methylanthranilamide (1.87 g, 11.4 mmol), 5-[4-[(2,2-diethoxy)ethoxy]phenyl methyl]thiazolidin-2,4-dione (2.0 g, 5.8 mmol) obtained in example 2 and PPE (9.86 g, 22.8 mmol) by a similar procedure to that described in example 3. mp: 201.9° C.

Method B

The title compound (340 mg, 64%) was obtained from 5-[4-[[1,3-dimethyl-4-oxo-1,2,3,4-tetrahydro-2-quinazolinyl]methoxy] phenyl methylene]thiazolidin-2,4-dione (500 mg) obtained in example 9 by a similar procedure to that described in example 2.

$^1$H NMR (CDCl$_3$): δ8.76 (bs, 1H, D$_2$O exchangeable), 7.94 (d, J=7.50 Hz, 1H), 7.38 (t, J=7.50 Hz, 1H), 7.10 (d, J=8.30 Hz, 2H), 6.86 (t, J=7.50 Hz, 1H), 6.71 (d, J=8.30 Hz, 2H), 6.62 (d, J=7.50 Hz, 1H), 4.87 (t, J=5.81 Hz, 1H), 4.45 (dd, J=9.04, 3.83 Hz, 1H), 4.20–4.00 (m, 2H), 3.38 (dd, J=14.02, 3.83 Hz, 1H), 3.23 (s, 3H), 3.12 (s, 3H), 3.10 (dd, J=14.02, 9.04 Hz, 1H).

EXAMPLE 12

5-[4-[[3-Methyl-4-oxo-1,2,3,4-tetrahydro-2-quinazolinyl]methoxy]phenyl methyl]thiazolidin-2,4-dione:

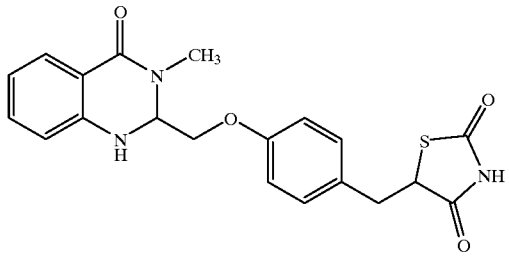

Method A

The title compound (0.96 g, 95%) was prepared from 5-[4-[[3-methyl-4-oxo-3,4-dihydro-2-quinazolinyl]methoxy]phenyl methylene]thiazolidin-2,4-dione (1.0 g) (preparation described in copending U.S. application Ser. Nos. 08/777,627 and 08/884,816), by a similar procedure to that described in example 2.

Method B

The title compound (350 mg, 44%) was obtained from N-methyl anthranilamide (272 mg, 2.0 mmol) and 5-[4-[(2,2-diethoxy)ethoxy]phenyl methyl]thiazolidin-2,4-dione (746 mg, 2.2 mmol) obtained from example 2 and PPE (1.73 g, 4.0 mmol) by a similar procedure to that described in example 3. mp: 86–90° C.

Method C

The title compound (480 mg, 96%) was prepared from 5-[4-[[3-methyl-4-oxo-3,4-dihydro-2-quinazolinyl]methoxy]phenyl methyl]thiazolidin-2,4-dione (500 mg) (preparation described in copending U.S. application Ser. Nos. 08/777,627 and 08/884,816), by a similar procedure to that described in example 2.

Method D

The title compound (440 mg, 88%) was prepared from 5-[4-[[3-methyl-4-oxo-1,2,3,4-tetrahydro-2-quinazolinyl]methoxy]phenyl methylene]thiazolidin-2,4-dione (500 mg) obtained in example 10, by a similar procedure to that described in example 2.

$^1$H NMR (CDCl$_3$): δ8.23 (bs, 1H, D$_2$O exchangeable), 7.95 (d, J=7.50 Hz, 1H), 7.43 (t, J=7.50 Hz, 1H), 7.12 (d, J=8.54 Hz, 2H), 7.08 (t, J=7.50 Hz, 1H), 6.93 (d, J=7.50 Hz, 1H), 6.77 (d, J=8.54 Hz, 2H), 5.62 (t, J=5.39 Hz, 1H), 4.48 (dd, J=9.04, 3.74 Hz, 1H), 4.32–4.08 (m, 2H), 3.45 (dd, J=14.05, 3.74 Hz, 1H), 3.20 (d, J=3.83 Hz, 3H), 3.10 (dd, J=14.05, 9.04 Hz, 1H).

EXAMPLE 13

5-[4-[[3-Ethyl-1-methyl-4-oxo-1,2,3,4-tetrahydro-2-quinazolinyl]methoxy]phenyl methyl]thiazolidin-2,4-dione:

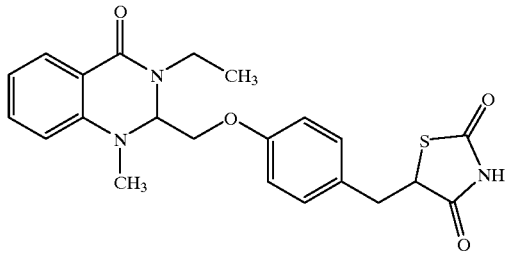

The title compound (1.6 g, 65%) was obtained from 2-(N-methyl)amino-N-ethyl benzamide (1.08 g, 6.06 mmol) and 5-[4-[(2,2-diethoxy)ethoxy]phenyl methyl]thiazolidin-2,4-dione (2.26 g, 6.68 mmol) obtained in example 2 and PPE (5.23 g, 12.13 mmol) by a similar procedure to that described in example 3. mp: 72–74° C.

$^1$H NMR (CDCl$_3$): δ11.99 (bs, 1H, D$_2$O exchangeable), 7.69 (d, J=7.50 Hz, 1H), 7.36 (t, J=7.50 Hz, 1H), 7.09 (d, J=8.30 Hz, 2H), 6.78 (t, J=7.50 Hz, 1H), 6.76 (d, J=8.30 Hz, 2H), 6.68 (d, J=7.50 Hz, 1H), 5.18 (t, J=5.30 Hz, 1H), 4.84 (dd, J=8.62, 4.47 Hz, 1H) 4.05 (q J=7.05 Hz, 2H), 4.12–3.80 (m, 2H), 3.36 (dd, J=14.05, 4.47 Hz, 1H), 3.06 (s, 3H), 3.13 (dd, J=14.05 8.62 Hz, 1H), 1.18 (t, J=7.05 Hz, 3H).

EXAMPLE 14

5-[4-[[1-Methyl-4-oxo-1,2,3,4-tetrahydro-2-quinazolinyl]methoxy] phenyl methyl]thiazolidin-2,4-dione:

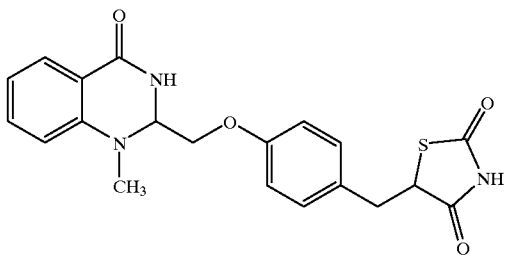

The title compound (450 mg, 23%) was obtained from 2-(N-methyl)amino benzamide (750 mg, 5.0 mmol) and 5-[4-[(2,2-diethoxy)ethoxy]phenyl methyl]thiazolidin-2,4-dione (1.87 g, 5.51 mmol) obtained in example 2 and PPE (4.33 g, 10.02 mmol) by a similar procedure to that described in example 3. mp: 108–110° C.

$^1$H NMR (CDCl$_3$): δ10.10 (bs, 1H, D$_2$O exchangeable), 7.93 (d, J=7.50 Hz, 1H), 7.42 (t, J=7.50 Hz, 1H), 7.09 (d, J=8.53 Hz, 2H), 6.84 (t, J=7.50 Hz, 1H), 6.73 (d, J=8.53 Hz, 2H), 6.64 (d, J=7.50 Hz, 1H), 4.98 (t, J=4.56 Hz, 1H), 4.43 (dd, J=8.90, 3.97 Hz, 1H), 4.20–3.82 (m, 2H), 3.37 (dd, J=14.11, 3.97 Hz, 1H), 3.12 (dd, J=14.11, 8.90 Hz, 1H), 3.10 (s, 3H).

EXAMPLE 15

5-[4-[[1,3-Dimethyl-4-oxo-1,2,3,4-tetrahydro-2-quinazolinyl]methoxy] phenyl methyl]thiazolidin-2,4-dione, sodium salt:

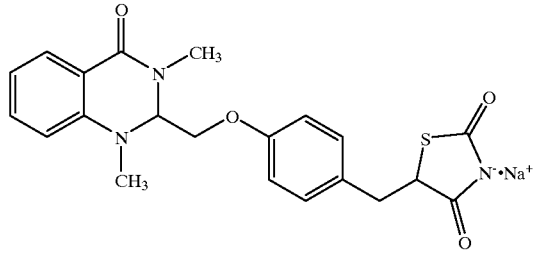

The title compound (150 mg, 95%) was obtained from 5-[4-[[1,3-dimethyl-4-oxo-1,2,3,4-tetrahydro-2-quinazolinyl]methoxy]phenyl methyl]thiazolidin-2,4-dione (150 mg, 0.36 mmol) obtained in example 11, by a similar procedure described in example 7. mp: 281–237° C.

$^1$H NMR (CDCl$_3$): δ7.72 (d, J=7.50 Hz, 1H), 7.40 (t, J=7.50 Hz, 1H), 7.10 (d, J=8.30 Hz, 2H), 6.90–6.66 (m, 4H), 5.20 (t, J=5.30 Hz, 1H), 4.20–4.05 (m, 3H), 3.32 (dd, J=13.53, 3.23 Hz, 1H), 3.13 (s, 3H), 3.07 (s, 3H), 2.62 (dd, J=13.52, 10.70 Hz, 1H).

EXAMPLE 16

5-[4-[[4-Oxo-1,2,3,4-tetrahydro-2-quinazolinyl] methoxy] phenyl methyl]thiazolidin-2,4-dione

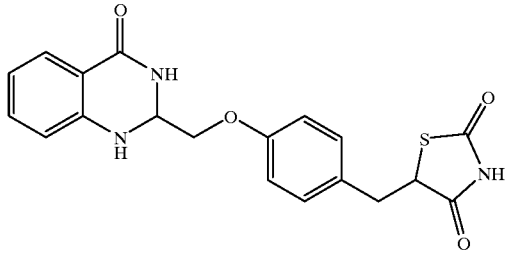

The title compound (0.42 g, 50%) was obtained from anthranilamide (0.3 g, 2.2 mmol) and 5-[4-[(2,2-diethoxy]ethoxy]phenyl methyl]thiazolidin-2,4-dione (0.82 g, 2.42 mmol) obtained in example 2 and PPE (1.91 g, 4.4 mmol) by a similar procedure to that described in example 3. m.p: 81–83° C.

$^1$H NMR (CDCl$_3$): δ8.59 (bs, 1H, D$_2$O exchangeable), 7.89, (d, J=7.70 Hz, 1H), 7.35 (t, J=7.50 Hz, 1H), 7.15 (d, J=8.62 Hz, 2H), 6.95–6.75 (m, 3H), 6.69 (d, J=7.50 Hz, 1H), 5.20 (t, J=5.70 Hz, 1H), 4.65 (bs, 1H, D$_2$O exchangeable), 4.49 (dd, J=9.03, 4.06 Hz, 1H), 4.20–4.10 (m, 1H), 4.10–3.92 (m, 1H), 3.40 (dd, J=14.12, 4.06 Hz, 1H), 3.18 (dd, J=14.12, 9.03 Hz, 1H).

EXAMPLE 17

5-[4-[[1,3-Diethyl-4-oxo-1,2,3,4-tetrahydro-2-quinazolinyl] methoxy] phenyl methyl]thiazolidin-2,4-dione

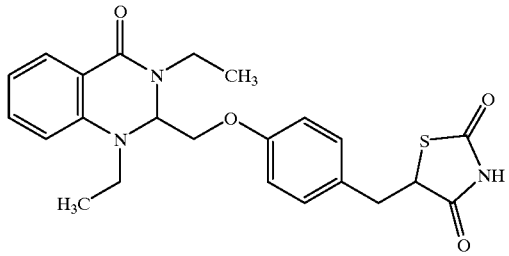

The title compound (0.4 g, 53%) was obtained from N,N'-diethylanthranilamide (0.32 g, 1.66 mmol) and 5-[4-[(2,2-diethoxy]ethoxy]phenyl methyl]thiazolidin-2,4-dione (0.62 g, 1.83 mmol) obtained in example 2 and PPE (1.44 g, 3.37 mmol) by a similar procedure to that described in example 3. m.p: 74–76° C.

$^1$H NMR (CDCl$_3$): δ8.60 (bs, 1H, D$_2$O exchangeable), 7.95, (d, J=7.50 Hz, 1H), 7.36 (t, J=7.50 Hz, 1H), 7.09 (d, J=8.60 Hz, 2H), 6.86 (t, J=7.57 Hz, 1H), 6.75 (d, J=7.50 Hz, 1H), 6.71 (d, J=8.60 Hz, 2H), 4.92 (t, J=5.81 Hz, 1H), 4.46 (dd, J=9.13, 3.73 Hz, 1H), 4.20–3.90 (m, 3H), 3.90–3.00 (m, 5H), 1.45–1.15 (m, 6H).

EXAMPLE 18

5-[4-[[1-Ethyl-3-methyl-4-oxo-1,2,3,4-tetrahydro-2-quinazolinyl] methoxy] phenyl methyl]thiazolidin-2,4-dione

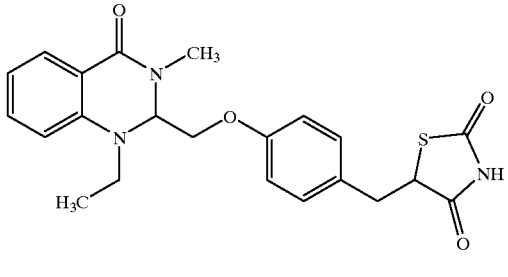

The title compound (575 mg, 52%) was obtained from N-ethyl-N'-methylanthranilamide (460 mg, 2.58 mmol) and 5-[4-[(2,2-diethoxy]ethoxy]phenyl methyl]thiazolidin-2,4-dione (963 mg, 2.8 mmol) obtained in example 2 and PPE (1.91 g, 4.4 mmol) by a similar procedure to that described in example 3. m.p: 165° C.

$^1$H NMR (CDC$_3$): δ8.30 (bs, 1H, D$_2$O exchangeable), 7.96 (d, J=7.50 Hz, 1H), 7.38 (t, J=7.50 Hz, 1H), 7.11 (d, J=8.50 Hz, 2H), 6.88 (t, J=7.50 Hz, 1H), 6.76 (d, J=7.50 Hz, 1H), 6.72 (d, J=8.50 Hz, 2H), 4.89 (t, J=5.80 Hz, 1H), 4.47 (dd, J=8.36, 3.78 Hz, 1H), 4.10–3.95 (m, 2H), 3.70–3.50 (m, 1H), 3.50–3.30 (m, 2H), 3.24 (d, J=3.72, 3H), 3.20–3.00 (m, 1H), 1.30 (t, J=7.06 Hz, 3H).

EXAMPLE 19

5-[4-[[1-Ethyl-4-oxo-1,2,3,4-tetrahydro-2-quinazolinyl] methoxy] phenyl methyl]thiazolidin-2,4-dione

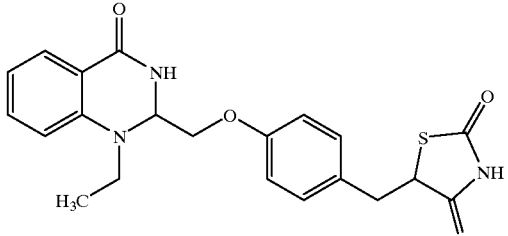

The title compound (240 mg, 43%) was obtained from N-ethyl anthranilamide (300 mg, 1.83 mmol) and 5-[4-[(2,2-diethoxy]ethoxy]phenyl methyl]thiazolidin-2,4-dione (680 mg, 2.0 mmol) obtained in example 2 and PPE (1.58 g, 3.65 mmol) by a similar procedure to that described in example 3. m.p: 77–79° C.

$^1$H NMR (CDCl$_3$): δ9.40 (bs, 1H, D$_2$O exchangeable), 7.95 (d, J=7.50 Hz, 1H), 7.39 (t, J=7.50 Hz, 1H), 7.09 (d, J=8.50 Hz, 2H), 6.95–6.65 (m, 4H), 4.99 (t, J=5.70 Hz, 1H), 4.44 (dd, J=8.30, 3.00 Hz, 1H), 4.15–3.90 (m, 2H), 3.75–3.50 (m, 1H), 3.50–3.25 (m, 2H) 3.20–3.00 (m, 1H), 1.30 (t, J=7.48 Hz, 3H).

Mutation in colonies of laboratory animals and different sensitivities to dietary regimens have made the development of animal models with non-insulin dependent diabetes associated with obesity and insulin resistance possible. Genetic models such as db/db and ob/ob (See Diabetes, (1982) 31(1): 1–6) in mice and fa/fa and zucker rats have been developed by the various laboratories for understanding the pathophysiology of disease and testing the efficacy of new antidiabetic compounds (Diabetes, (1983) 32: 830–838 ; Annu.

Rep. Sankyo Res. Lab. (1994) 46: 1–57). The homozygous animals, C57 BL/KsJ-db/db mice developed by Jackson Laboratory, US, are obese, hyperglycemic, hyperinsulinemic and insulin resistant (J. Clin. Invest., (1990) 85: 962–967), whereas heterozygous are lean and normoglycemic. In db/db model, mouse progressively develops insulinopenia with age, a feature commonly observed in late stages of human type II diabetes when blood sugar levels are insufficiently controlled. The state of pancreas and its course vary according to the models. Since this model resembles that of type II diabetes mellitus, the compounds of the present invention were tested for blood sugar and triglycerides lowering activities.

The compounds of the present invention showed blood sugar and triglycerides lowering activities through improved insulin resistance. This was demonstrated by the following in vivo experiments.

Male C57BL/KsJ-db/db mice of 8 to 14 weeks age, having body weight range of 35 to 60 grams, procured from the Jackson Laboraotory, USA, were used in the experiment. The mice were provided with standard feed (National Institute of Nutrition, Hyderabad, India) and acidified water, ad libitum. The animals having more than 300 mg/dl blood sugar were used for testing. The number of animals in each group was 4.

The random blood sugar and triglyceride levels were measured by collecting blood (100 μl) through orbital sinus, using heparinised capillary in tubes containing EDTA which was centrifuged to obtain plasma. The plasma glucose and triglycerides levels were measured spectrometrically, by glucose oxidase and glycerol-3-$PO_4$ oxidase/peroxidase enzyme (Dr. Reddy's Lab. Diagnostic Division Kits, Hyderabad, India) methods respectively. On 6th day the blood samples were collected one hour after administration of test compounds/vehicle for assessing the biological activity.

Test compounds were suspended on 0.25% carboxymethyl cellulose and administered to test group at a dose of 1 mg to 100 mg/kg through oral gavage daily for 6 days. The control group received vehicle (dose 10 ml/kg). Troglitazone (100 mg/kg, daily dose) was used as a standard drug which showed 28% reduction in random blood sugar level on 6th day.

The blood sugar and triglycerides lowering activities of the test compound was calculated according to the formula:

$$\text{Blood sugar/triglycerides lowering activity (\%)} = 1 - \frac{DT/DC}{TC/ZC} \times 100$$

ZC=Zero day control group value
DC=Zero day treated group value
TC=Control group value on test day
DT=Treated group value on the test day No adverse effects were observed for any of the mentioned compounds of invention in the above test. The compounds of the present invention also showed cholesterol lowering activity in the experimental animals used.

| Compound | Dose (mg/kg/day) | Maximum reduction in blood glucose level (%) | Triglyceride lowering (%) |
|---|---|---|---|
| Example 12 | 3 | 55 | 35 |
| Example 11 | 1 | 34 | 28 |
| Example 4 | 10 | 48 | 42 |
| Example 3 | 10 | 41 | 48 |

The experimental results from the db/db mice suggest that the novel compounds of the present invention also possess therapeutic utility as a prophylactic or regular treatment for obesity, cardiovascular disorders such as hypertension, hyperlipidaemia and other diseases; as it is known from the literature that such diseases are interrelated to each other.

We claim:

1. A compound of formula (I)

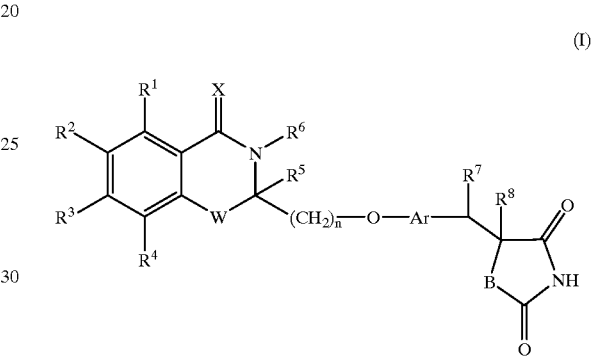

its tautomeric forms, its stereoisomers, its polymorphs, its pharmaceutically acceptable salts or its pharmaceutically acceptable solvates, wherein X represents O or S; $R^1$, $R^2$, $R^3$, and $R^4$ are the same or different and represent hydrogen, halogen, hydroxy, cyano, nitro; or optionally substituted groups selected from alkyl, ($C_3$–$C_6$)cycloalkyl, alkoxy, ($C_3$–$C_6$)cycloalkyloxy, aryl, aralkyl, heteroaryl, heteroaralkyl, heterocyclyl selected from aziridinyl, pyrrolidinyl, morpholinyl, piperidinyl or piperazinyl; aryloxy, alkoxycarbonyl, aryloxycarbonyl, aralkoxycarbonyl, alkylamino, arylamino, amino, aminoalkyl, hydroxyalkyl, alkoxyalkyl, thioalkyl, alkylthio, acyl, acylamino, aryloxycarbonylamino, aralkoxycarbonylamino, alkoxycarbonylamino, carboxylic acid or its derivatives, acyloxy, sulfonic acid or its derivatives; W represents a group $NR^9$; $R^6$ and $R^9$ are the same or different and represent hydrogen; or optionally substituted groups selected from alkyl, ($C_3$–$C_6$)cycloalkyl, aryl; aralkyl, heterocyclyl selected from aziridinyl, pyrrolidinyl, morpholinyl, piperidinyl, or piperazinyl; heteroaryl, heteroaralkyl, acyl, hydroxyalkyl, aminoalkyl, alkoxycarbonyl, aryloxycarbonyl, aralkoxycarbonyl, alkoxyalkyl, alkylthio, or thioalkyl groups; $R^5$ represents hydrogen, hydroxy or halogen or optionally substituted groups selected from alkyl, aryl, heteroaryl, acyl, alkoxy, aralkyl, or aralkoxy; n is an integer ranging from 1–4; Ar represents an optionally substituted divalent aromatic or heterocyclic group, $R^7$ and $R^8$ are the same or different and individually represent hydrogen, halogen, hydroxy, lower alkyl, optionally substituted aralkyl, or together form a bond; and B represents an oxygen atom or a sulfur atom.

2. A compound as claimed in claim 1, wherein substituents of the groups $R^1$, $R^2$, $R^3$ or $R^4$ are selected from halogen, hydroxy, cyano, nitrol; or optionally substituted groups selected from alkyl, ($C_3$–$C_6$) cycloalkyl, alkoxy, ($C_3$–$C_6$) cycloalkoxy, aryl, aralkyl, heterocyclyl selected from aziridinyl, pyrrolidinyl, morpholinyl, piperidinyl, or piperazinyl; heteroaryl, heteroaralkyl, acyl, acyloxy, hydroxyalkyl, amino, acylamino, arylamino, aminoalkyl, aryloxy, alkoxycarbonyl, alkylamino, alkoxyalkyl, alkylthio, thioalkyl groups, carboxylic acid or its derivatives, or sulfonic acid or its derivatives.

3. A compound as claimed in claim 1, wherein substituents of the groups represented by $R^6$ and $R^9$ are selected from hydroxy, halogen, acyl, acyloxy or amino groups.

4. A compound as claimed in claim 1, wherein Ar represents substituted or unsubstituted divalent phenylene, naphthylene, pyridyl, quinolinyl, benzofuryl, dihydrobenzofuryl, benzopyranyl, indolyl, indolinyl, azaindolyl, azaindolinyl, pyrazolyl, benzothiazolyl or benzoxazolyl.

5. A compound according to claim 4, wherein substituents of the group represented by Ar are selected from linear or branched ($C_1$–$C_6$)alkyl, ($C_1$–$C_3$)alkoxy, halogen, acyl, amino, acylamino, thio; or carboxylic acids or sulfonic acids or their derivatives.

6. A pharmaceutical composition which comprises a compound of formula (I)

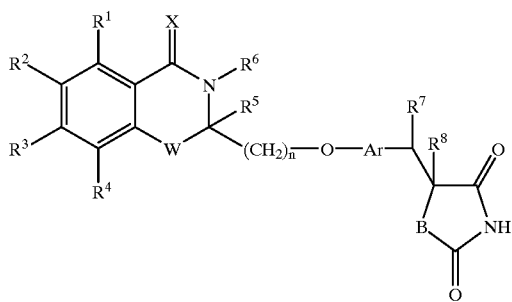

(I)

as defined in claim 1 and a pharmaceutically acceptable carrier, diluent, excipient or solvate.

7. A pharmaceutical composition as claimed in claim 6, in the form of a tablet, capsule, powder, syrup, solution or suspension.

8. A process for preparing a compound of formula (I)

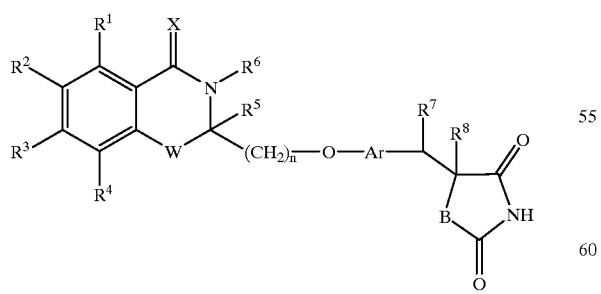

(I)

its tautomeric forms, its stereoisomers, its polymorphs, its pharmaceutically acceptable salts or its pharmaceutically acceptable solvates, wherein X represents O or S; $R^1$, $R^2$, $R^3$, and $R^4$ are the same or different and represent hydrogen, halogen, hydroxy, cyano, nitro; or optionally substituted groups selected from alkyl, ($C_3$–$C_6$) cycloalkyl, alkoxy, ($C_3$–$C_6$) cycloalkyloxy, aryl, aralkyl, heteroaryl, heteroaralkyl, heterocyclyl selected from aziridinyl, pyrrolidinyl, morpholinyl, piperidinyl, or piperazinyl; aryloxy, alkoxycarbonyl, aryloxycarbonyl, aralkoxycarbonyl, alkylamino, arylamino, amino, aminoalkyl, hydroxyalkyl, alkoxyalkyl, thioalkyl, alkylthio, acyl, acylamino, aryloxycarbonylamino, aralkoxycarbonylamino, alkoxycarbonylamino, carboxylic acid or its derivatives, acyloxy, sulfonic acid or its derivatives; W represents a group $NR^9$, $R^6$ and $R^9$ are the same or different and represents hydrogen; or optionally substituted groups selected from alkyl, ($C_3$–$C_6$) cycoalkyl, aryl, aralkyl, heterocyclyl selected from aziridinyl, pyrrolidinyl, morpholinyl, piperidinyl, or piperazinyl; heteroaryl; heteroaralkyl, acyl, hydroxyalkyl, aminoalkyl, alkoxycarbonyl, aryloxycarbonyl, aralkoxycarbonyl, alkoxyalkyl, alkylthio, or thioalkyl groups; $R^5$ represents hydrogen, hydroxy or halogen atom or optionally substituted groups selected from alkyl, aryl, heteroaryl, acyl, alkoxy, aralkyl, or aralkoxy; n is an integer ranging from 1–4; Ar represents an optionally substituted divalent aromatic or heterocyclic group, $R^7$ and $R^8$ are the same or different and individually represent hydrogen, halogen, hydroxy, lower alkyl, optionally substituted aralkyl group or together form a bond; B represents an oxygen atom or a sulfur atom; comprising the steps of:

a) reacting a compound of formula (XIII)

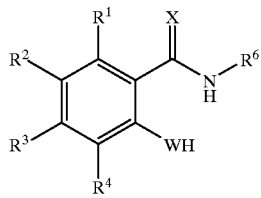

(XIII)

where all symbols are as defined above, with a compound of formula (XIV)

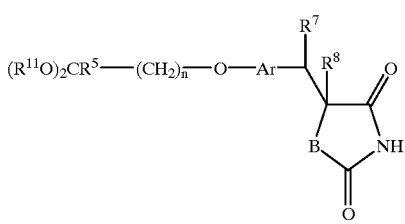

(XIV)

where $R^{11}$ is a linear or branched ($C_1$–$C_5$) alkyl and all other symbols are as defined above and optionally, b) converting the compound of formula (I) obtained into its pharmaceutically acceptable salts, or its pharmaceutically acceptable solvates.

9. A compound of formula (I)

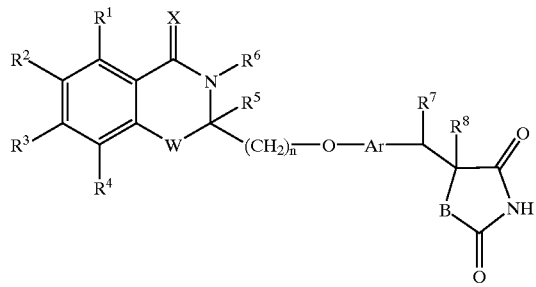

its tautomeric forms, its stereoisomers, its polymorphs, its pharmaceutically acceptable salts or its pharmaceutically acceptable solvates, wherein X represents O or S; $R^1, R^2, R^3$, and $R^4$ are the same or different and represent hydrogen, halogen, hydroxy, cyano, nitro; or optionally substituted groups selected from alkyl, $(C_3-C_6)$ cycloalkly, alkoxy, $(C_3-C_6)$cycloalkyloxy, aryl, aralkyl, heteroaryl, heteroaralkyl, heterocyclyl, alkoxycarbonyl, aryloxycarbonyl, aralkoxycarbonyl, alkylamino, arylamino, amino, aminoalkyl, hydroxyalkyl, alkoxyalkyl, thioalkyl, alkylthio, acyl, acylamino, aryloxycarbonylamino, aralkoxycarbonylamino, alkoxycarbonylamino, carboxylic acid or its derivatives, acyloxy, sulfonic acid or its derivatives; W represents a group $NR^9$; $R^6$ and $R^9$ are the same or different and represents hydrogen; or optionally substituted groups selected from alkyl, $(C_3-C_6)$ cycloalkyl, aryl, aralkyl, heterocyclyl selected from aziridinyl, pyrrolidinyl, morpholinyl, piperidinyl, or piperazinyl; heteroaryl, heteroaralkyl, acyl, hydroxyalkyl, aminoalkyl, alkoxycarbonyl, aryloxycarbonyl, aralkoxycarbonyl, alkoxyalkyl, alkylthio, or thioalkyl groups; $R^5$ represents hydrogen, hydroxy or halogen or optionally substituted groups selected from alkyl, aryl, heteroaryl selected from, acyl, alkoxy, aralkyl, or aralkoxy; n is an integer ranging from 1–4; Ar represents an optionally substituted divalent aromatic or heterocyclic group, $R^7$ and $R^8$ are the same or different and individually represent hydrogen, halogen, hydroxy, lower alkyl, optionally substituted aralkyl, or together form a bond; and B represents an oxygen atom or a sulfur atom prepared by the process of claim 8.

10. A compound of formula (I)

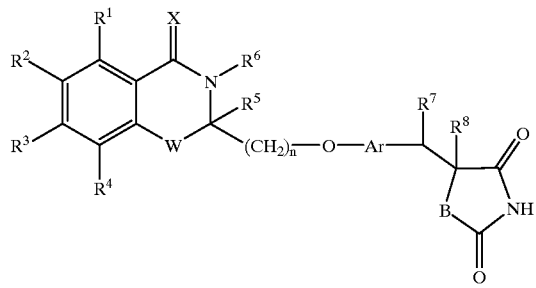

its tautomeric forms, its stereoisomers, its polymorphs, its pharmaceutically acceptable salts or its pharmaceutically acceptable solvates, wherein X represents O or S; $R^1, R^2, R^3$, and $R^4$ are the same or different and represent hydrogen, halogen, hydroxy, cyano, nitro; or optionally substituted groups selected from alkyl, $(C_3-C_6)$cycloalkyl, alkoxy, $(C_3-C_6)$cycloalkyloxy, aryl, aralkyl, heteroaryl, heteroaralkyl, heterocyclyl selected from aziridinyl, pyrrolidinyl, morpholinyl, piperidinyl or piperazinyl; aryloxy, alkoxycarbonyl, aryloxycarbonyl, aralkoxycarbonyl, alkylamino, arylamino, amino, aminoalkyl, hydroxyalkyl, alkoxyalkyl, thioalkyl, alkylthio, acyl, acylamino, aryloxycarbonylamino, aralkoxycarbonylamino, alkoxycarbonylamino, carboxylic acid or its derivatives, acyloxy or sulfonic acid or its derivatives; W represents a group $NR^9$; $R^6$ and $R^9$ are the same or different and represents hydrogen; or optionally substituted groups selected from alkyl, $(C_3-C_6)$ cycloalkyl, aryl, aralkyl, heterocyclyl selected from aziridinyl, pyrrolidinyl, morpholinyl, piperidinyl, or piperazinyl; heteroaryl, heteroaralkyl, acyl, hydroxyalkyl, aminoalkyl, alkoxycarbonyl, aryloxycarbonyl, aralkoxycarbonyl, alkoxyalkyl, alkylthio, or thioalkyl groups; $R^5$ represents hydrogen, hydroxy or halogen or optionally substituted groups selected from alkyl, aryl, heteroaryl, acyl, alkoxy, aralkyl, or aralkoxy; n is an integer ranging from 1–4; Ar represents an optionally substituted divalent aromatic or heterocyclic group, $R^7$ and $R^8$ are the same or different and individually represent hydrogen, halogen, hydroxy, lower alkyl, optionally substituted aralkyl, or together form a bond; and B represents an oxygen atom or a sulfur atom prepared by the process comprising the steps of:

a) reacting a compound of formula (XIV)

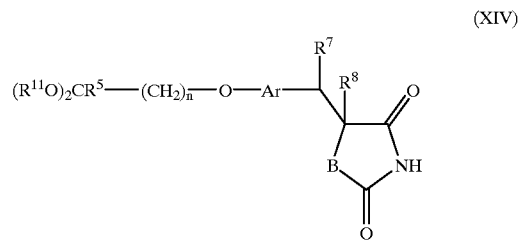

wherein $R^5$ represents hydrogen, halogen, hydroxy or optionally substituted alkyl, aryl, heteroaryl, acyl, alkoxy, aralkyl, or aralkoxy; n is an integer ranging from 1–4; Ar represents an optionally substituted divalent aromatic or heterocyclic group; B represents an oxygen atom or a sulfur atom and $R^{11}$ is a linear or branched $(C_1-C_5)$ alkyl group with a compound of formula (XIII)

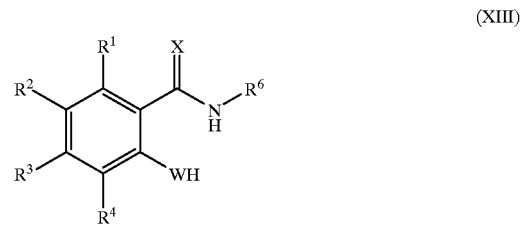

where all symbols are as defined above to yield a compound of formula (VIII)

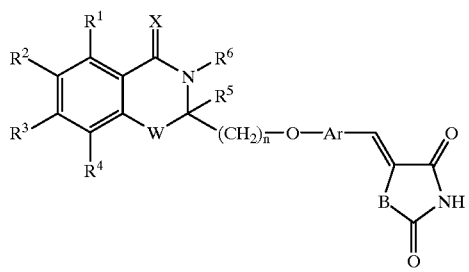

(VIII)

where $R^1$, $R^2$, $R^3$, $R^4$, $R^5$, $R^6$, X, W, n, and Ar are as defined above and B represents sulfur or oxygen and optionally ii) reducing the compound of formula (VIII) to obtain a compound of formula (IX),

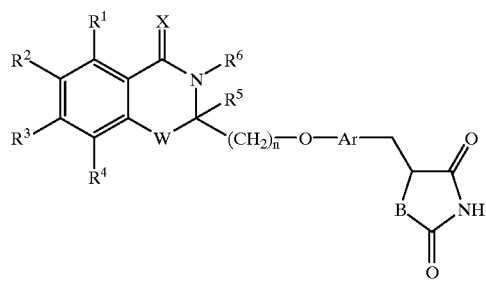

(IX)

or b) reacting a compound of formula (XIII)

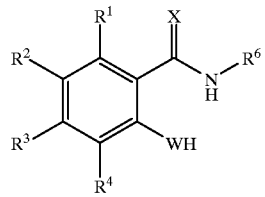

(XIII)

where all symbols are defined above, with a compound of formula (XIV)

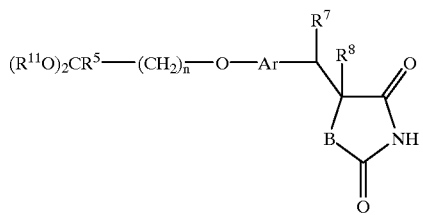

(XIV)

where all symbols are defined above and optionally, ii) converting the compound of formula (1) obtained into its pharmaceutically acceptable salts, or its pharmaceutically acceptable solvates.

11. A compound of formula (I)

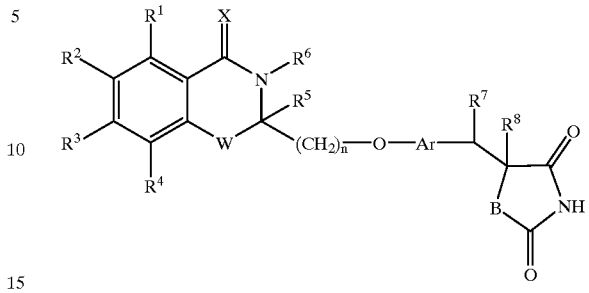

(I)

its tautomeric forms, its stereoisomers, its polymorphs, its pharmaceutically acceptable salts or its pharmaceutically acceptable solvates, wherein X represents O or S; $R^1$, $R^2$, $R^3$, and $R^4$ are the same or different and represent hydrogen, halogen, hydroxy, cyano, nitro; or optionally substituted groups selected from alkyl, ($C_3$–$C_6$) cycloalkyl, alkoxy, ($C_3$–$C_6$) cycloalkyloxy, aryl, aralkyl, heteroaryl, heteroaralkyl, heterocyclyl selected from aziridinyl, pyrrolidinyl, morpholinyl, piperidinyl or piperazinyl; aryloxy, alkoxycarbonyl, aryloxycarbonyl, aralkoxycarbonyl, alkylamino, arylamino, amino, aminoalkyl, hydroxyalkyl, alkoxyalkyl, thioalkyl, alkylthio, acyl, acylamino, aryloxycarbonylamino, aralkoxycarbonylamino, alkoxycarbonylamino, carboxylic acid or its derivatives, acyloxy or sulfonic acid or its derivatives; W represents a group $NR^9$; $R^6$ and $R^9$ are the same or different and represents hydrogen; or optionally substituted groups selected from alkyl, ($C_3$–$C_6$)cycloalkyl, aryl, aralkyl, heterocyclyl selected from aziridinyl, pyrrolidinyl, morpholinyl, piperidinyl, or piperazinyl; heteroaryl, heteroaralkyl, acyl, hydroxyalkyl, aminoalkyl, alkoxycarbonyl, aryloxycarbonyl, aralkoxycarbonyl, alkoxyalkyl, alkylthio, or thioalkyl groups; $R^5$ represents hydrogen, hydroxy or halogen or optionally substituted groups selected from alkyl, aryl, heteroaryl, acyl, alkoxy, aralkyl, or aralkoxy; n is an integer ranging from 1–4; Ar represents an optionally substituted divalent aromatic or heterocyclic group, $R^7$ and $R^8$ are the same or different and individually represent hydrogen, halogen, hydroxy, lower alkyl, optionally substituted aralkyl, or together form a bond; and B represents an oxygen atom or a sulfur atom prepared by the process which comprises the steps of:

a) i) reacting the intermediate of formula (III)

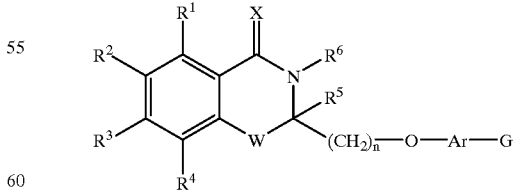

(III)

where G represents CHO group and all other groups are as defined above with 2,4-thiazolidinedione or 2,4-oxazolidinedione, (ii) removing the water formed during the reaction to yield a compound of formula (VIII)

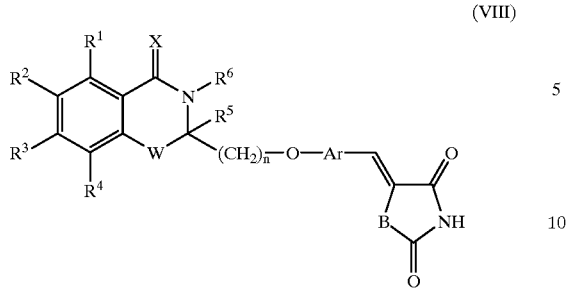
(VIII)

where $R^1, R^2, R^3, R^4, R^5, R^6, X, W, n,$ and Ar are as defined above and B represents sulfur or oxygen;

iii) reducing the compound of formula (VIII) obtained above to obtain a compound of formula (IX)

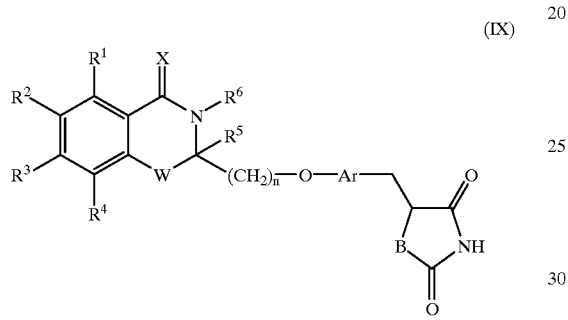
(IX)

wherein $R^1, R^2, R^3, R^4, R^5, R^6, X, W, n,$ Ar and B are as defined above, and if needed, iv) converting the compound of formula (VIII) and (XI) obtained above into their pharmaceutically acceptable salts, or their pharmaceutically acceptable solvates; or b) reacting a compound of formula (XI)

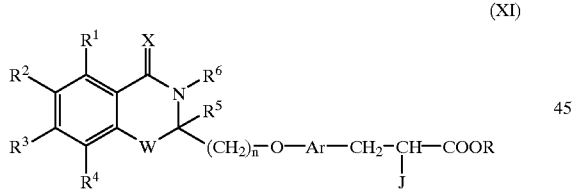
(XI)

wherein $R^1, R^2, R^3, R^4, R^5, R^6, X, W, n$ and Ar are as defined above, J is a halogen atom and R is a lower alkyl group, with thiourea followed by treatment with an acid; or c) reacting a compound of formula (IV)

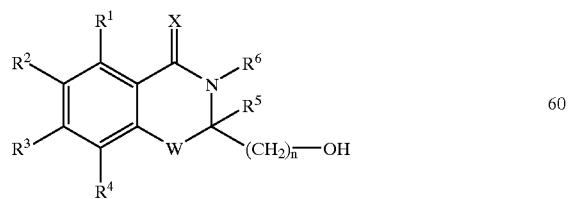

where $R^1, R^2, R^3, R^4, R^5, R^6, X, W$ and n are as defined above, with a compound of formula (X)

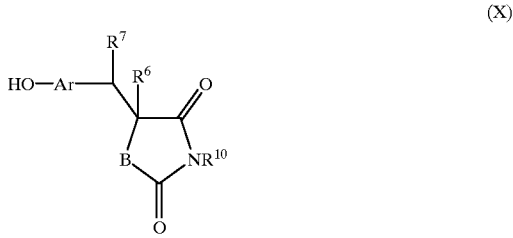
(X)

where $R^7, R^8,$ Ar and B are as defined above and $R^{10}$ represents hydrogen atom or a nitrogen protecting group or d) reacting a compound of formula (VI)

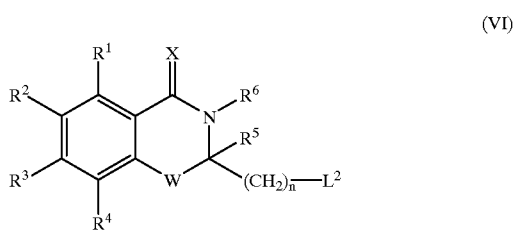
(VI)

where $R^1, R^2, R^3, R^4, R^5, R^6, X, W$ and n are as defined above and L is a halogen atom or a leaving group with a compound of formula (X)

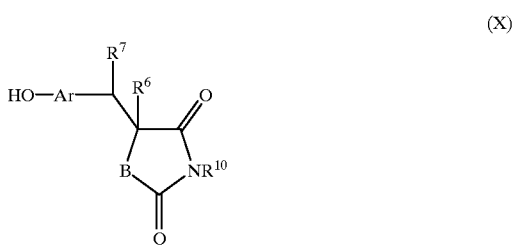
(X)

where $R^7, R^8,$ B; and $R^{10}$ are as defined above.

12. A compound according to claim 1, which is selected from the group consisting of the following compounds:

5-[4-[[1,3-Dimethyl-4-oxo-1,2,3,4-tetrahydro-2-quinazolinyl]methoxy]phenyl methylene] thiazolidin-2,4-dione;

5-[4-[[3-Methyl-4-oxo-1,2,3,4-tetrahydro-2-quinazolinyl]methoxy]phenyl methylene]thiazolidin-2, 4,dione;

5-[4-[[1,3-Dimethyl-4-oxo-1,2,3,4-tetrahydro-2-quinazolinyl]methoxy]phenyl methyl] thiazolidin-2,4-dione;

5-[4-[[3-Methyl-4-oxo-1,2,3,4-tetrahydro-2-quinazolinyl]methoxy]phenyl methyl]thiazolidin-2,4-dione;

5-[4-[[3-Ethyl-1-methyl-4-oxo-1,2,3,4-tetrahydro-2-quinazolinyl]methoxy]phenylmethyl]thiazolidin-2,4-dione;

5-[4-[[1-Methyl-4-oxo-1,2,3,4-tetrahydro-2-quinazolinyl]methoxy]phenyl methyl]thiazolidin-2,4-dione;

5-[4-[[1,3-Dimethyl-4-oxo-1,2,3,4-tetrahydro-2-quinazolinyl]methoxy]phenyl methyl] thiazolidin-2,4-dione, sodium salt;

5-[4-[[4-oxo-1,2,3,4-tetrahydro-2-quinazolinyl]methoxy] phenylmethyl]thiazolidin-2,4-dione;

5-[4-[[1,3-Diethyl-4-oxo-1,2,3,4-tetrahydro-2-quinazolinyl]methoxy]phenyl methyl] thiazolidin-2,4-dione;

5-[4-[[1-Ethyl-3-methyl-4-oxo-1,2,3,4-tetrahydro-2-quinazolinyl]methoxy]phenylmethyl]thiazolidin-2,4-dione; and 5-[4-[[1-Ethyl-4-oxo-1,2,3,4-tetrahydro-2-quinazolinyl] methoxy]phenyl methyl]thiazolidin-2,4-dione.

13. A pharmaceutical composition which comprises, a compound according to claim 12, and a pharmaceutically acceptable carrier, diluent or excipient.

14. A pharmaceutical composition according to claim 13, in the form of a tablet, capsule, powder, syrup, solution or suspension.

15. An intermediate of formula (III)

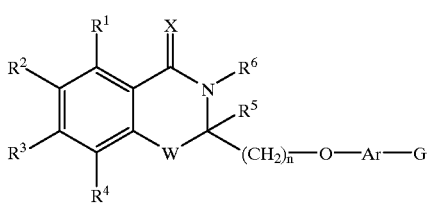

(III)

wherein X represents O or S; the groups $R^1$, $R^2$, $R^3$, and $R^4$ are the same or different and represent hydrogen, halogen, hydroxy, cyano, nitro; or optionally substituted groups selected from alkyl, ($C_3$–$C_6$)cycloalkyl, alkoxy, ($C_3$–$C_6$) cycloalkyloxy, aryl, aralkyl, heteroaryl, heteroaralkyl, heterocyclyl selected from aziridinyl, pyrrolidinyl, morpholinyl, piperidinyl, or piperazinyl; aryloxy, alkoxycarbonyl, aryloxycarbonyl, aralkoxycarbonyl, alkylamino, arylamino, amino, aminoalkyl, hydroxyalkyl, alkoxyalkyl, thioalkyl, alkylthio, acyl, acylamino, aryloxycarbonylamino, aralkoxycarbonylamino, alkoxycarbonylamino, carboxylic acid or its derivatives, acyloxy, or sulfonic acid or its derivatives; W represents a group $N^9$; $R^6$ and $R^9$ are the same or different and represent hydrogen; or optionally substituted groups selected from alkyl, ($C_3$–$C_6$) cycloalkyl, aryl, aralkyl, heterocyclyl selected from aziridinyl, pyrrolidinyl, morpholinyl, piperidinyl, or piperazinyl; heteroaryl, heteroaralkyl, acyl, hydroxyalkyl, aminoalkyl, alkoxycarbonyl, aryloxycarbonyl, aralkoxycarbonyl, alkoxyalkyl, alkylthio, or thioalkyl groups; $R^5$ represents hydrogen, hydroxy or halogen or optionally substituted groups selected from alkyl, aryl, heteroaryl, acyl, alkoxy, aralkyl, or aralkoxy; n is an integer ranging from 1–4; Ar represents an optionally substituted divalent aromatic or heterocyclic group; G represents CHO, $NO_2$, —$NH_2$ or —$CH_2CH(J)$—COOR, where J represents a halogen atom and R represents H or lower alkyl group.

16. An intermediate of formula (III)

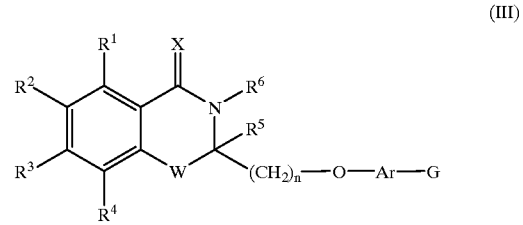

(III)

wherein X represents O or S; the groups $R^1$, $R^2$, $R^3$, and $R^4$ are the same or different and represent hydrogen, halogen, hydroxy, cyano, nitro; or optionally substituted groups selected from alkyl, ($C_3$–$C_6$)cycloalkyl, alkoxy, ($C_3$–$C_6$) cycloalkyloxy, aryl, aralkyl, heteroaryl, heteroaralkyl, heterocyclyl selected from aziridinyl, pyrrolidinyl, morpholinyl, piperidinyl, or piperazinyl; aryloxy, alkoxycarbonyl, aryloxycarbonyl, aralkoxycarbonyl, alkylamino, arylamino, amino, aminoalkyl, hydroxyalkyl, alkoxyalkyl, thioalkyl, alkylthio, acyl, acylamino, aryloxycarbonylamino, aralkoxycarbonylamino, alkoxycarbonylamino, carboxylic acid or its derivatives, acyloxy or sulfonic acid or its derivatives; W represents a group $NR^9$; $R^6$ and $R^9$ are the same or different and represent hydrogen; or optionally substituted groups selected from alkyl, ($C_3$–$C_6$)cycloalkyl, aryl, aralkyl, heterocyclyl selected from aziridinyl, pyrrolidinyl, morpholinyl, piperidinyl, or piperazinyl; heteroaryl, heteroaralkyl, acyl, hydroxyalkyl, aminoalkyl, alkoxycarbonyl, aryloxycarbonyl, aralkoxycarbonyl, alkoxyalkyl, alkylthio, or thioalkyl groups; $R^5$ represents hydrogen, hydroxy or halogen or optionally substituted groups selected from alkyl, aryl, heteroary, acyl, alkoxy, aralkyl, or aralkoxy; n is an integer ranging from 1–4; Ar represents an optionally substituted divalent aromatic or heterocyclic group; G represents CHO, $NO_2$, —$NH_2$ or —$CH_2CH(J)$—COOR, where J represents a halogen atom and R represents H or lower alkyl group prepared by the process comprising the steps of:

a) reacting a compound of formula (IV)

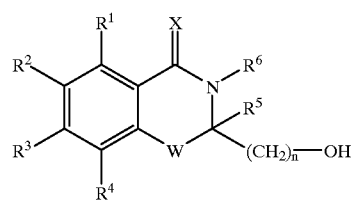

(IV)

wherein, $R^1$, $R^2$, $R^3$, $R^4$, $R^5$, $R^6$, X, W, and n are as defined above with a compound of formula (V)

(V)

where $L^1$ is a halogen atom, G is a CHO or a $NO_2$ group and Ar is as defined above; or b) reacting a compound of formula (VI)

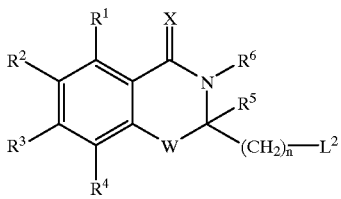

where $R^1, R^2, R^3, R^4, R^5, R^6, X, W$ and n are as defined above and $L^2$ is a halogen atom or leaving group with a compound of formula (VII)

where G is a CHO or $NO_2$ group and Ar is as defined above; or c) reacting a compound of formula (IV)

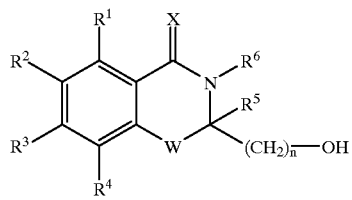

wherein, $R^1, R^2, R^3, R^4, R^5, R^6, X, W$ and n are as defined above, with a compound of formula (VII)

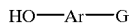

where G is a CHO or $NO_2$ group and Ar is as defined above; or d) diazotizating a compound of formula (XII)

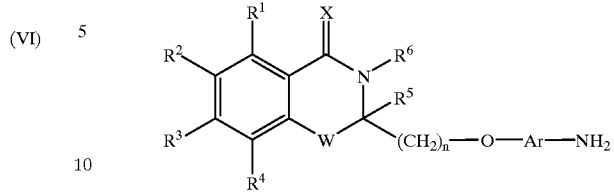

wherein, $R^1, R^2, R^3, R^4, R^5, R^6, X, W$, n and Ar are as defined above followed by treatment with acrylic acid ester in the presence of hydrohalo acids and copper oxide or copper halide to yield a compound of formula (III) where all symbols are as defined above and G represents $CH_2$—CH(J)—COOR group, where R represents lower alkyl group.

17. A method of preventing or treating diabetes caused by insulin resistance or impaired glucose tolerance or complications of diabetes said diabetes caused by insulin resistance or impaired glucose tolerance comprising administering a therapeutically effective amount of a compound of formula (I) as defined in claim 1, and a pharmaceutically acceptable carrier, diluent or excipient to a patient in need thereof.

18. A method according to claim 17 wherein the complication is dyslipidaemia, hypertension, coronary heart disease, cardiovascular disorders, atherosclerosis, obesity, psoriasis, polycystic ovarian syndrome (PCOS), renal diseases, diabetic nephropathy, glomerulonephritis, glomerular sclerosis, nephrotic syndrome, hypertensive nephrosclerosis, end-stage renal disease, microalbuminuria or eating disorders.

19. A method of reducing blood glucose, triglycerides or free fatty acids in a subject in need thereof comprising administering a therapeutically effective amount of a compound of formula (I), as defined in claim 1 and a pharmaceutically acceptable carrier, diluent or solvate.

20. A method of preventing or treating diabetes caused by insulin resistance or impaired glucose tolerance or complications of diabetes caused by insulin resistance or impaired glucose tolerance comprising administering a therapeutically effective amount of a compound of formula (I) as defined in claim 12 and a pharmaceutically acceptable carrier, diluent or excipient to a patient in need thereof.

21. A method according to claim 20 wherein the complication is dyslipdaemia, hypertension, coronary heart disease, cardiovascular disorders, atherosclerosis, obesity, psoriasis, polycystic ovarian syndrome (PCOS), renal diseases, diabetic nephropathy, glomerulonephritis, glomerular sclerosis, nephrotic syndrome, hypertensive nephrosclerosis, end-stage renal disease, microalbuminuria or eating disorders.

22. A method of reducing blood glucose, triglycerides or free fatty acids in a subject in need thereof comprising administering a therapeutically effective amount of a compound of formula (I), as defined in claim 12 and a pharmaceutically acceptable carrier, diluent or solvate.

* * * * *